(12) United States Patent
Balsells et al.

(10) Patent No.: US 8,308,167 B2
(45) Date of Patent: Nov. 13, 2012

(54) LOCKING MECHANISM WITH QUICK DISASSEMBLY MEANS

(75) Inventors: Pete J. Balsells, Newport Coast, CA (US); Farshid Dilmaghanian, Foothill Ranch, CA (US)

(73) Assignee: Bal Seal Engineering, Inc., Foothill Ranch, CA (US)

( * ) Notice: Subject to any disclaimer, the term of this patent is extended or adjusted under 35 U.S.C. 154(b) by 995 days.

(21) Appl. No.: 12/341,760

(22) Filed: Dec. 22, 2008

(65) Prior Publication Data
US 2009/0160139 A1 Jun. 25, 2009

Related U.S. Application Data

(60) Provisional application No. 61/015,915, filed on Dec. 21, 2007.

(51) Int. Cl.
*B23B 31/117* (2006.01)
(52) U.S. Cl. ......... 279/23.1; 279/89; 279/906; 285/318; 403/326; 403/372
(58) Field of Classification Search .................. 279/23.1, 279/24, 43, 79, 89, 906; 403/326, 372; 411/517; 285/318; 269/254 CS; *B23B 31/117*
See application file for complete search history.

(56) References Cited

U.S. PATENT DOCUMENTS

| | | | | |
|---|---|---|---|---|
| 659,523 A | * | 10/1900 | Furbish | 279/24 |
| 2,336,095 A | * | 12/1943 | Heding | 279/79 |
| 2,593,794 A | * | 4/1952 | Resina | 279/23.1 |
| 2,999,407 A | * | 9/1961 | De Frangesco | 173/211 |
| 3,610,063 A | * | 10/1971 | Hart | 474/94 |
| 3,819,194 A | * | 6/1974 | Grevich et al. | 279/23.1 |
| 4,678,210 A | * | 7/1987 | Balsells | 285/318 |
| 4,804,290 A | * | 2/1989 | Balsells | 403/326 |
| 4,805,943 A | | 2/1989 | Balsells | |
| 4,902,177 A | * | 2/1990 | Burnett | 409/234 |
| 4,906,031 A | * | 3/1990 | Vyse | 285/318 |
| 5,072,070 A | * | 12/1991 | Balsells | 174/370 |
| 5,079,388 A | * | 1/1992 | Balsells | 174/370 |
| 5,082,390 A | * | 1/1992 | Balsells | 403/326 |
| 5,091,606 A | * | 2/1992 | Balsells | 174/370 |
| 5,117,066 A | * | 5/1992 | Balsells | 174/370 |
| 5,226,682 A | * | 7/1993 | Marrison et al. | 285/308 |

(Continued)

FOREIGN PATENT DOCUMENTS

JP 09076105 A * 3/1997
(Continued)

OTHER PUBLICATIONS

International Search Report completed Jul. 30, 2009 and mailed Jul. 31, 2009 from corresponding International Application No. PCT/US2008/088064, filed Dec. 22, 2008 (7 pages).

(Continued)

*Primary Examiner* — Eric A Gates
(74) *Attorney, Agent, or Firm* — Klein, O'Neill & Singh, LLP

(57) ABSTRACT

A locking tool or device that permits rapid installation and removal of a removable component from a component that is fixed to a housing or equipment. The interchangeable, and hence removable, components may be held in place by individual holders that provide secure axial locking means and quick radial removal means requiring no axial space for the removal of such components from the main base tool.

26 Claims, 19 Drawing Sheets

U.S. PATENT DOCUMENTS

| | | | | |
|---|---|---|---|---|
| 5,411,348 A * | 5/1995 | Balsells | ................ | 403/326 |
| 5,474,309 A | 12/1995 | Balsells | | |
| 5,545,842 A * | 8/1996 | Balsells | ................ | 174/372 |
| 5,607,006 A * | 3/1997 | Koch | ................ | 164/112 |
| 5,727,821 A | 3/1998 | Miller | | |
| 6,789,826 B1 * | 9/2004 | Helgenberg et al. | ...... | 292/341.15 |
| 6,835,084 B2 * | 12/2004 | Poon et al. | ................ | 439/349 |
| 7,055,812 B2 * | 6/2006 | Balsells | ................ | 267/167 |
| 7,210,398 B2 * | 5/2007 | Balsells | ................ | 92/194 |
| 7,722,415 B2 * | 5/2010 | Chansrivong | ................ | 439/840 |
| 7,999,202 B2 * | 8/2011 | Fujita et al. | ................ | 200/275 |
| 8,057,270 B2 * | 11/2011 | Shimazu et al. | ................ | 439/827 |
| 8,167,285 B2 * | 5/2012 | Balsells | ................ | 267/166 |
| 2002/0122690 A1 * | 9/2002 | Poon et al. | ................ | 403/326 |
| 2003/0094812 A1 * | 5/2003 | Balsells | ................ | 285/318 |
| 2010/0029145 A1 * | 2/2010 | Balsells et al. | ................ | 439/827 |
| 2010/0090379 A1 * | 4/2010 | Balsells | ................ | 267/1.5 |
| 2010/0289198 A1 * | 11/2010 | Balsells et al. | ................ | 267/151 |

FOREIGN PATENT DOCUMENTS

| | | |
|---|---|---|
| KR | 20-2000-0010443 U | 6/2000 |
| KR | 10-2004-0101972 A | 12/2004 |
| WO | WO 2005-105207 | 11/2005 |

OTHER PUBLICATIONS

Written Opinion completed Jul. 30, 2009 and mailed Jul. 31, 2009 from corresponding International Application No. PCT/US2008/088064, filed Dec. 22, 2008 (4pages).

* cited by examiner

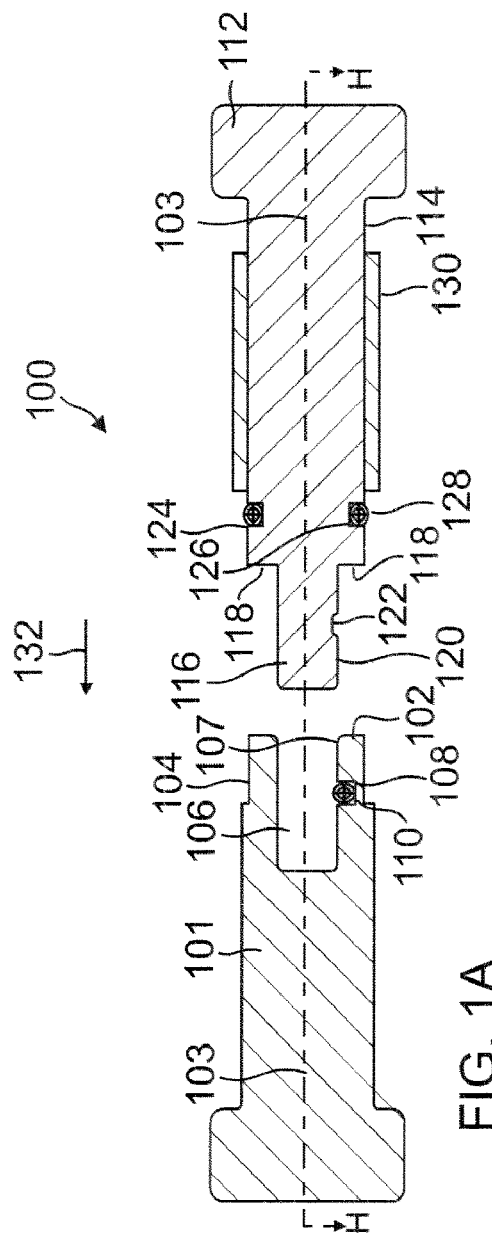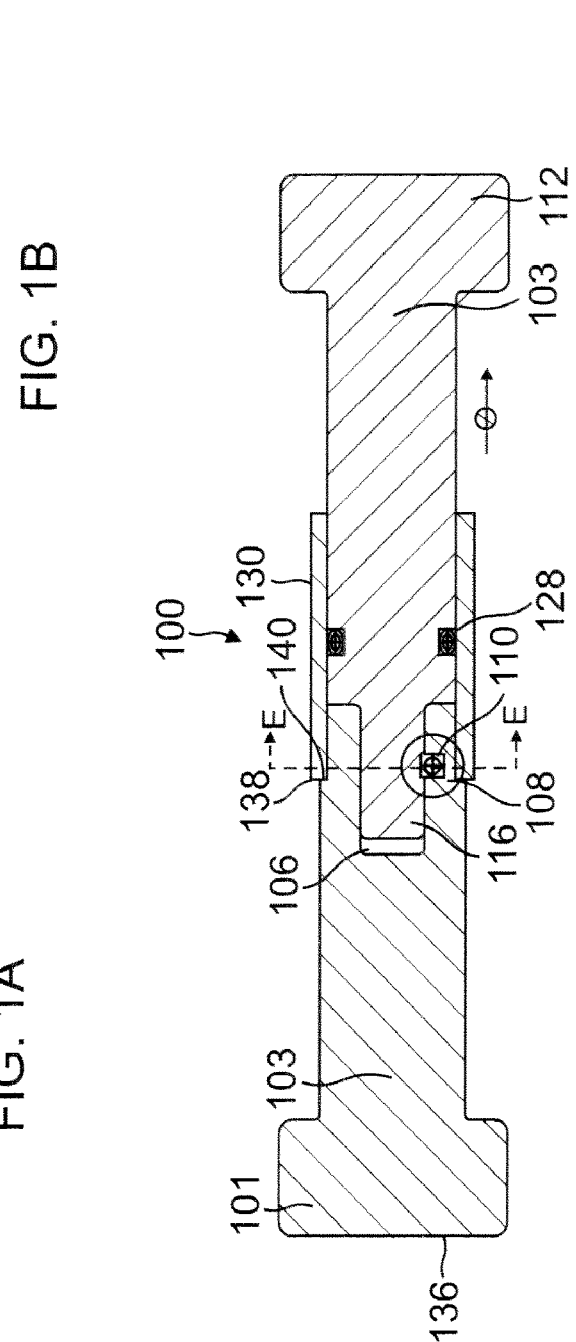

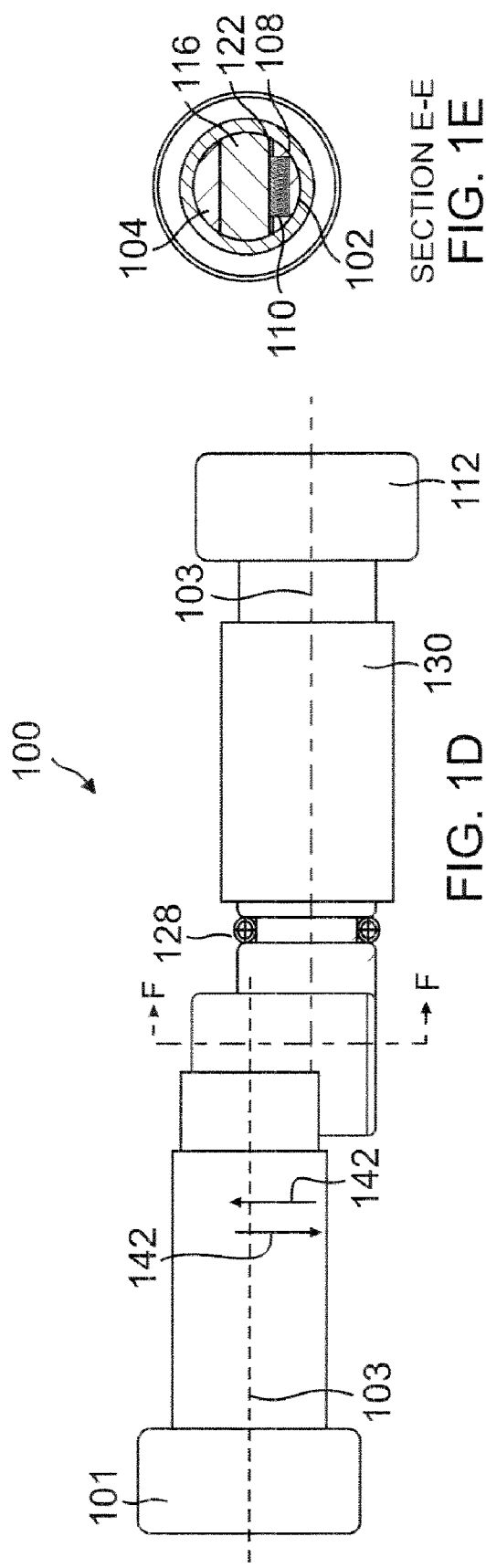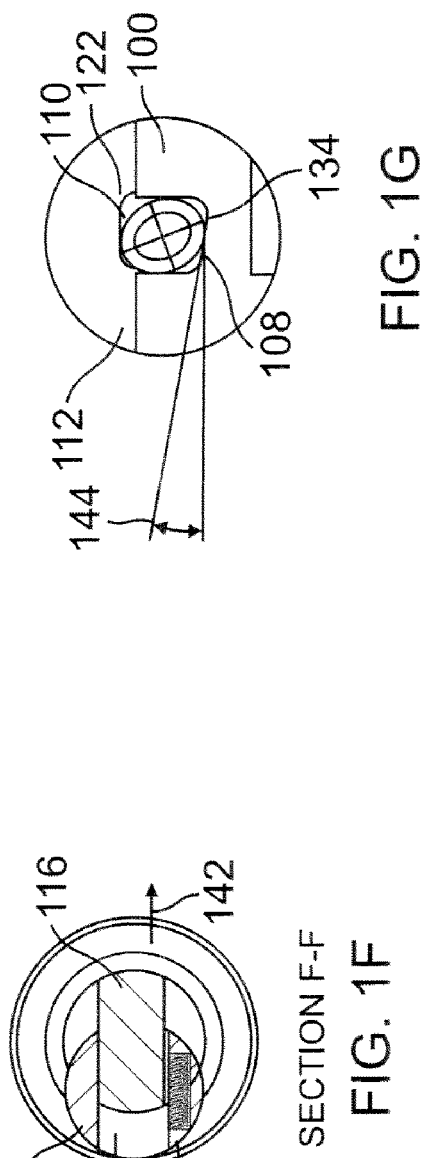

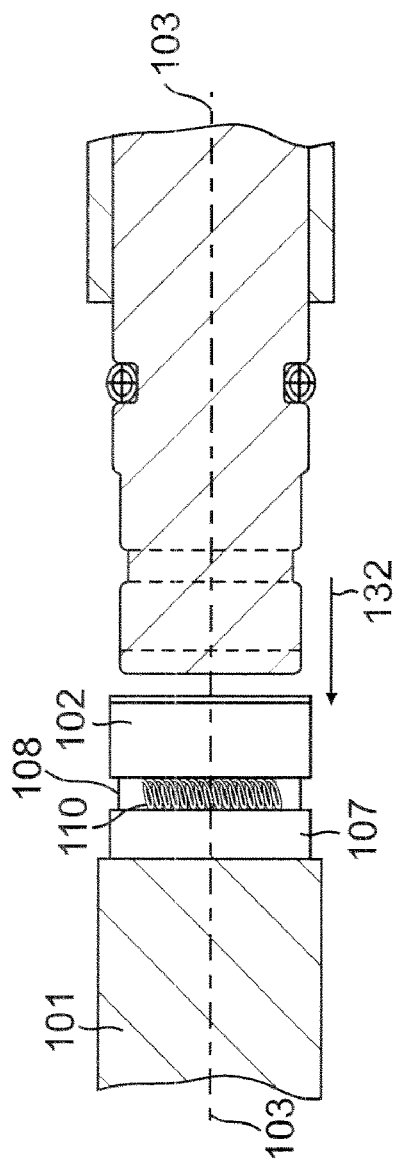
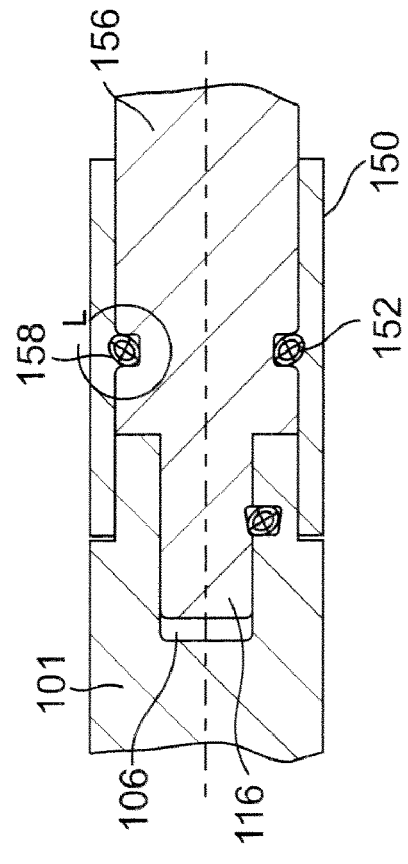
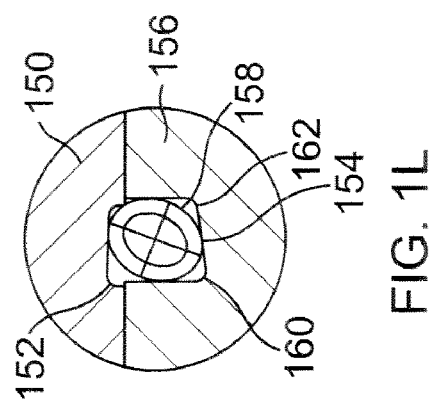

SECTION B-B

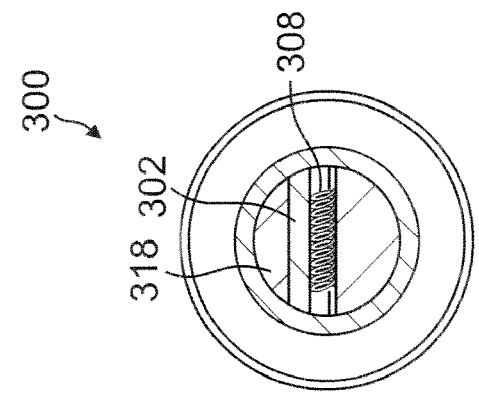
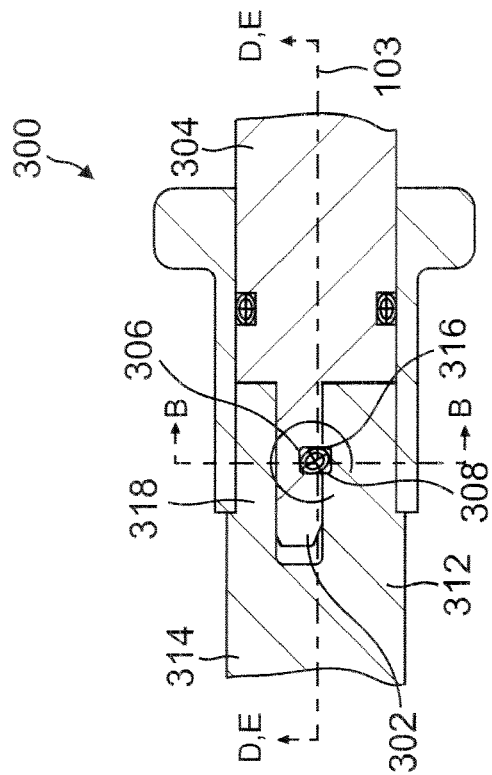
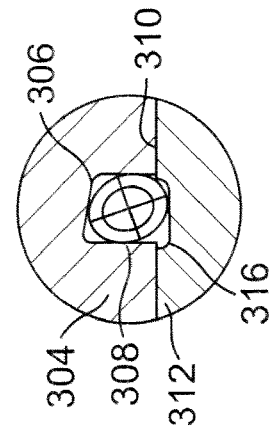
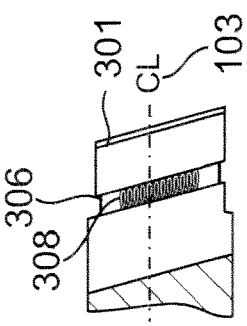
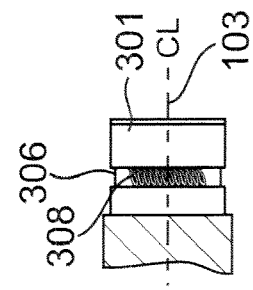

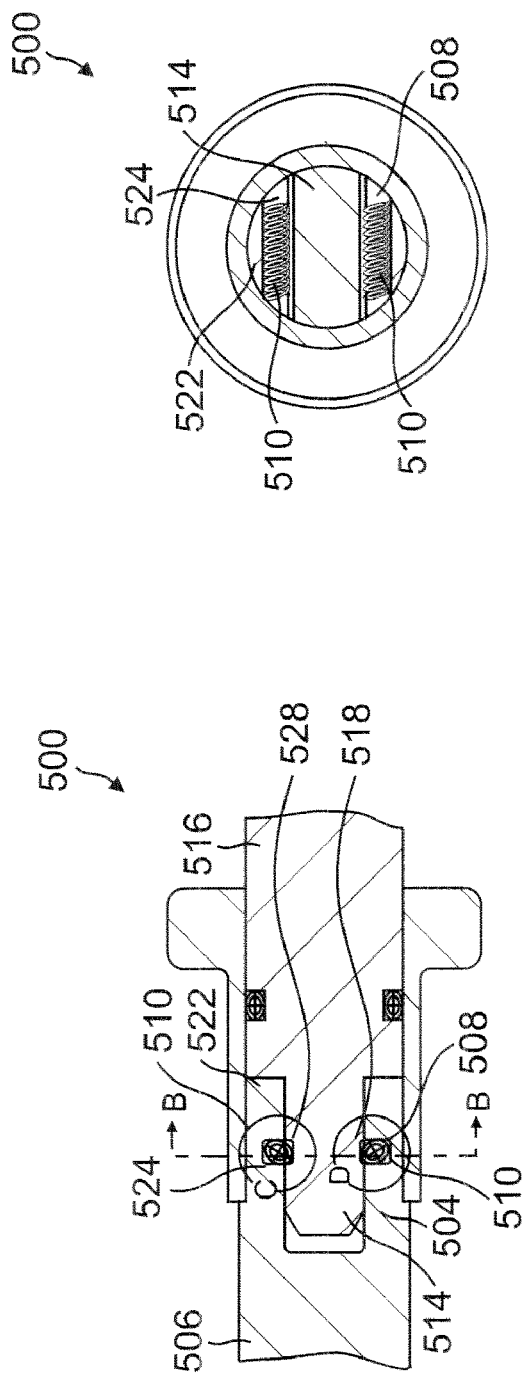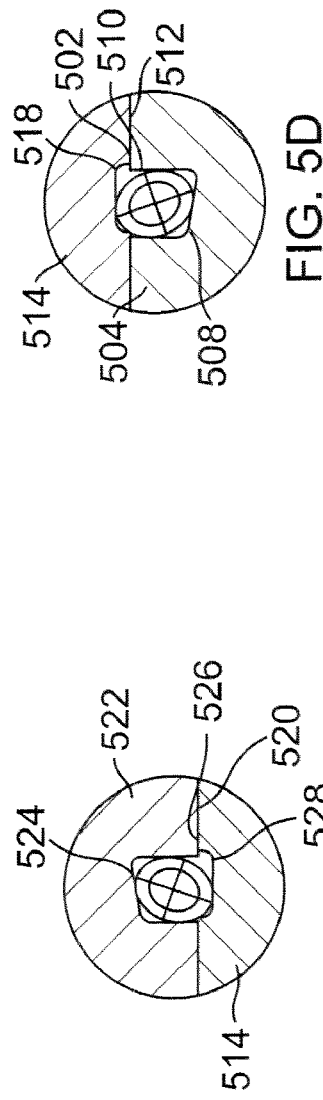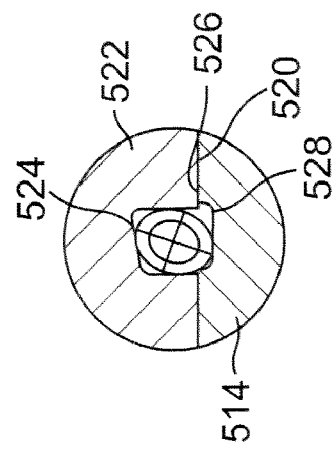

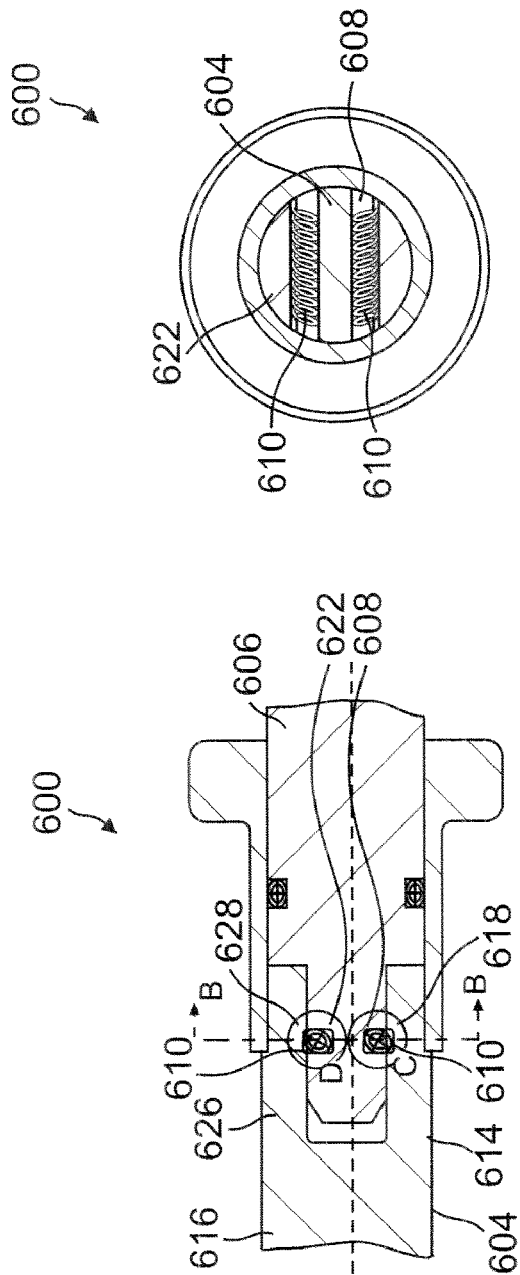
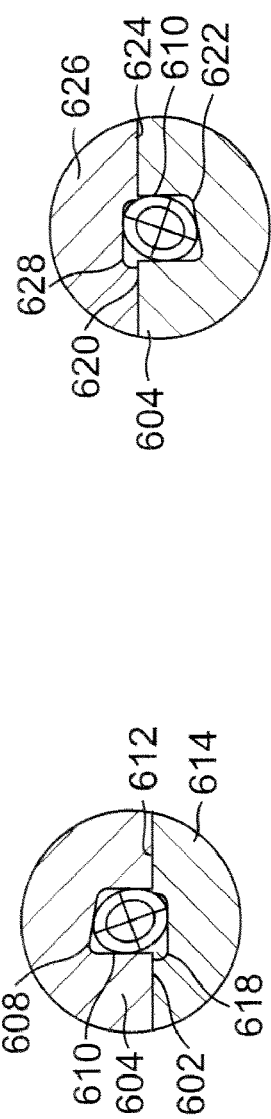
FIG. 6A
SECTION B-B FIG. 6B
FIG. 6C
FIG. 6D

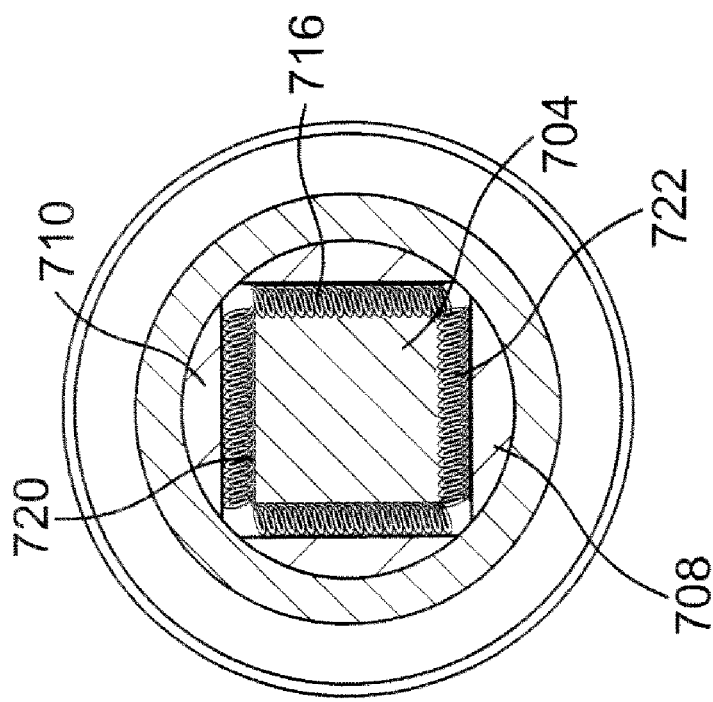
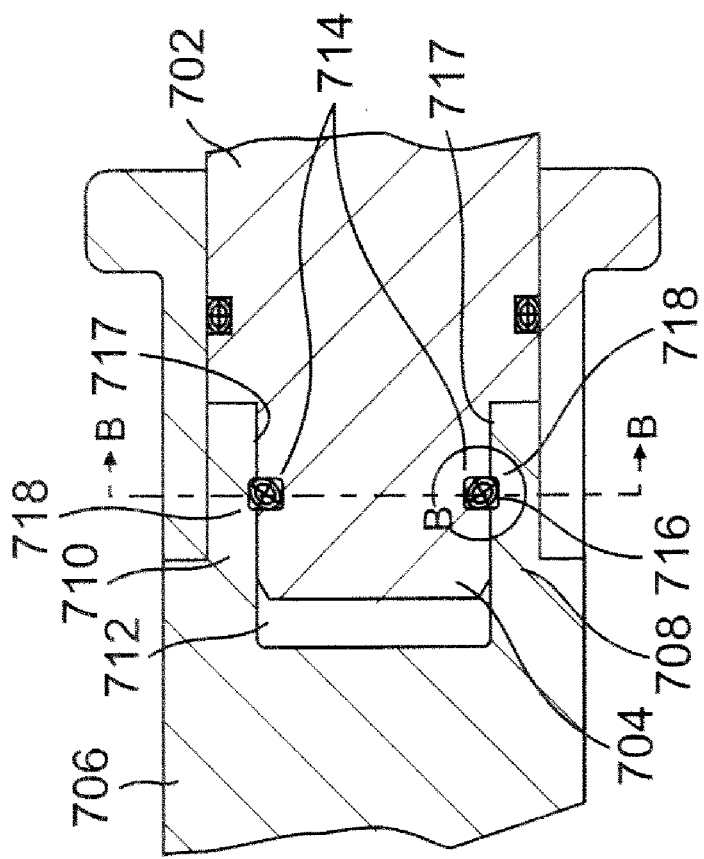
SECTION B-B
FIG. 7B
FIG. 7A

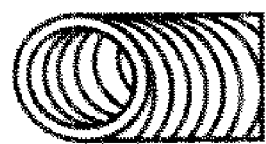
SECTION C-C
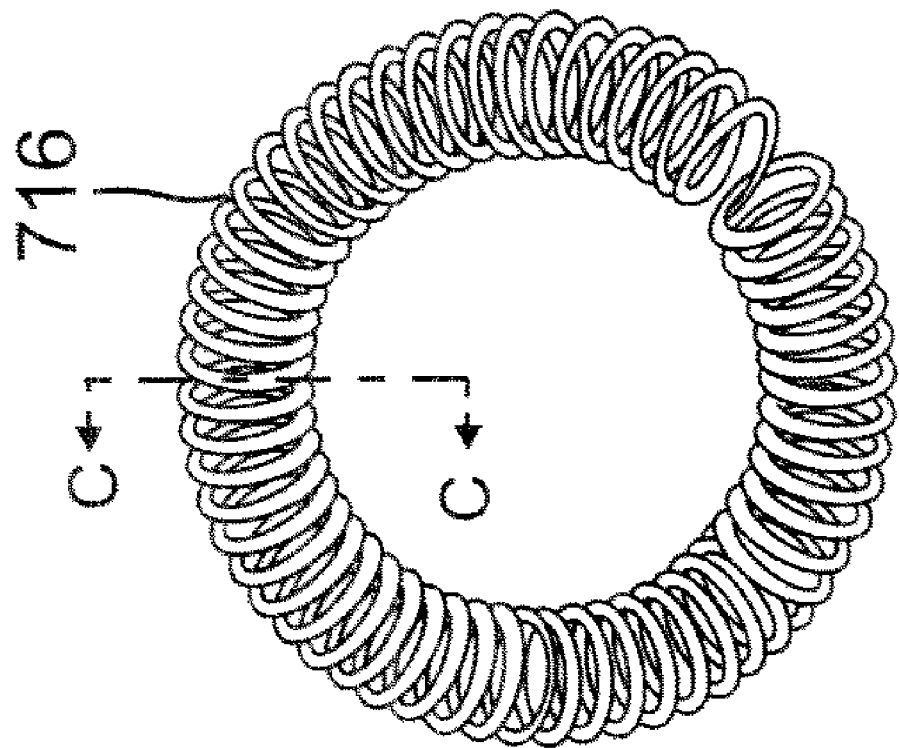
FIG. 7C

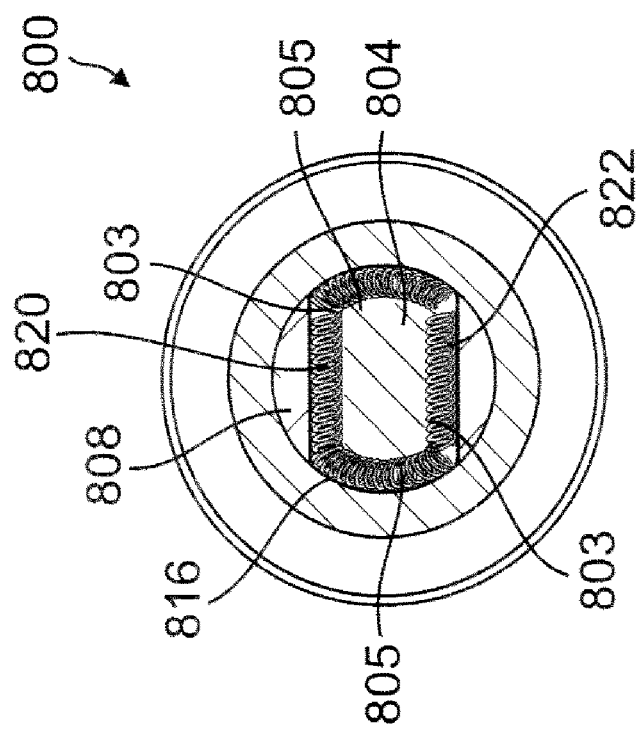
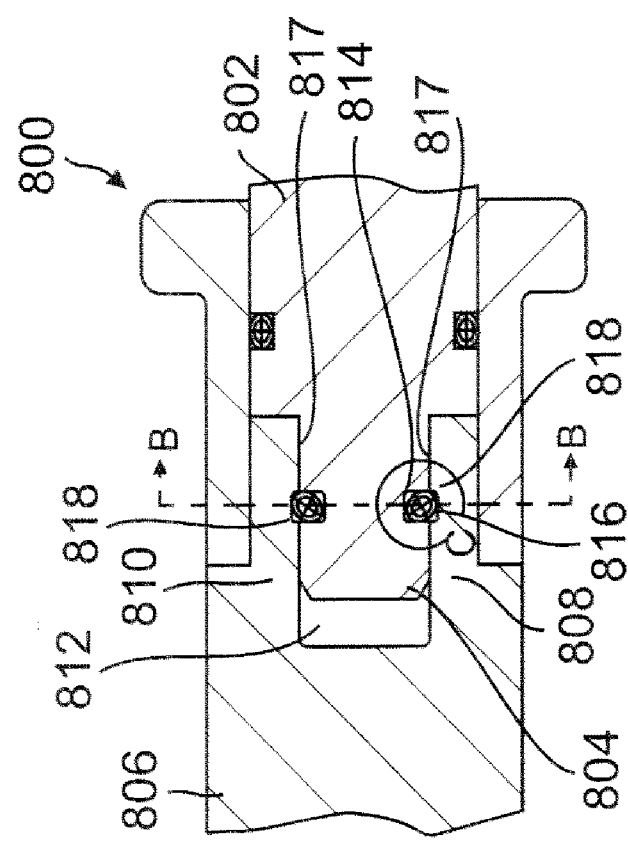

SECTION B-B

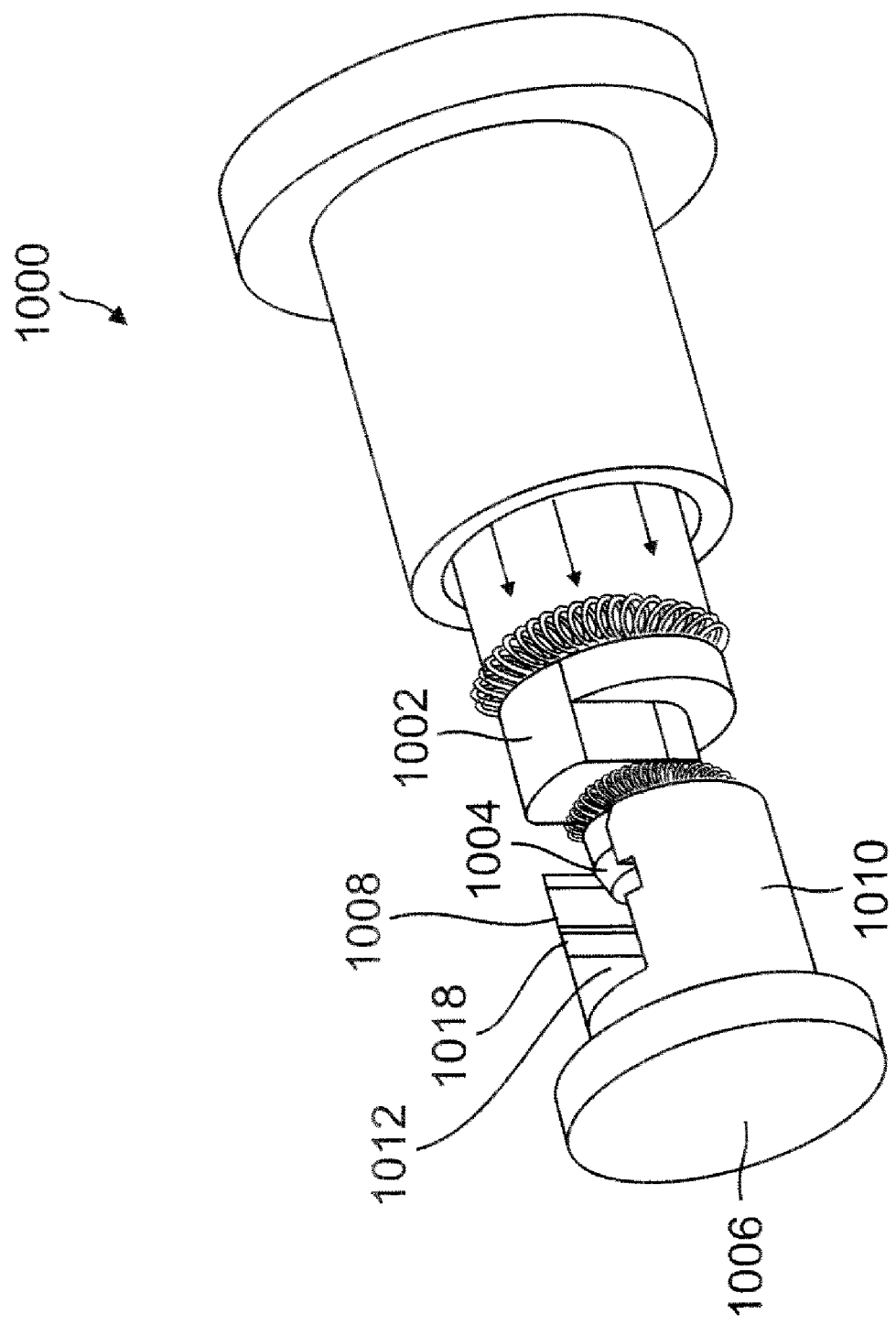

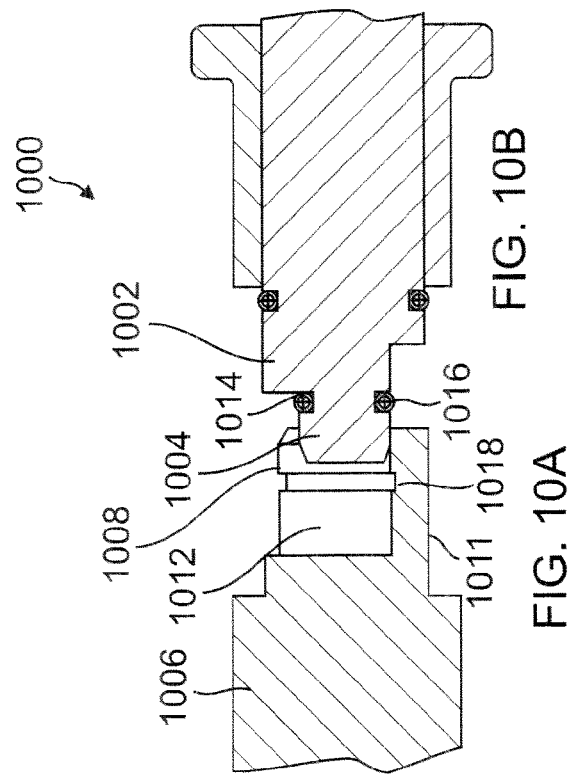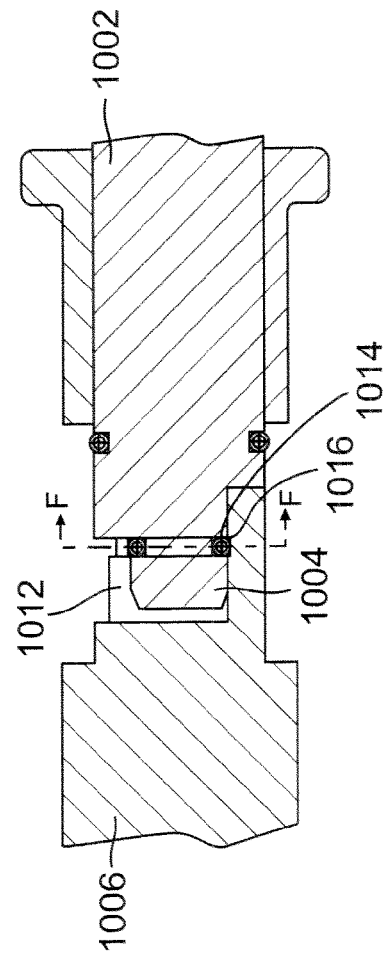

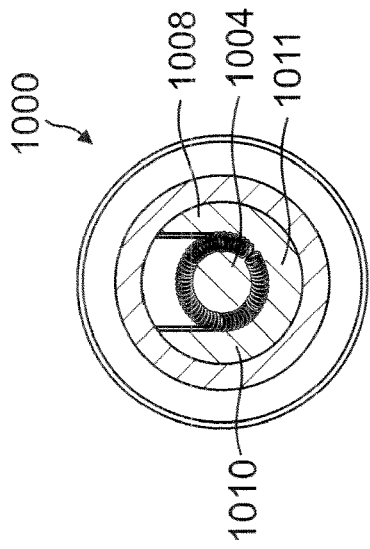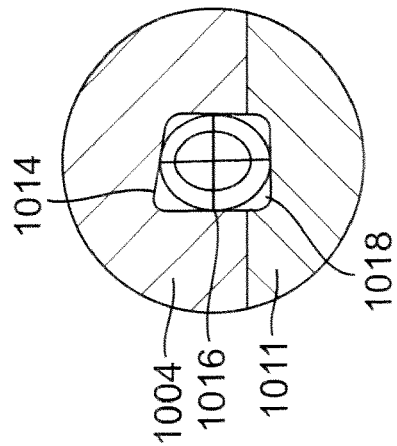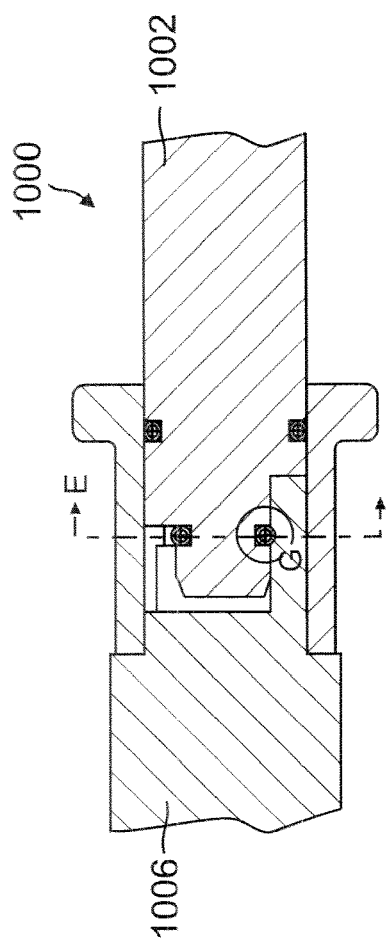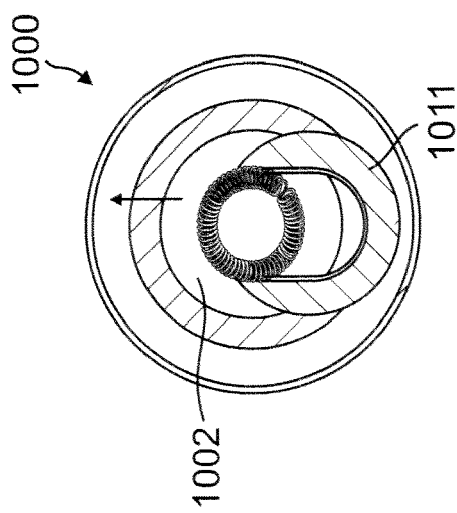

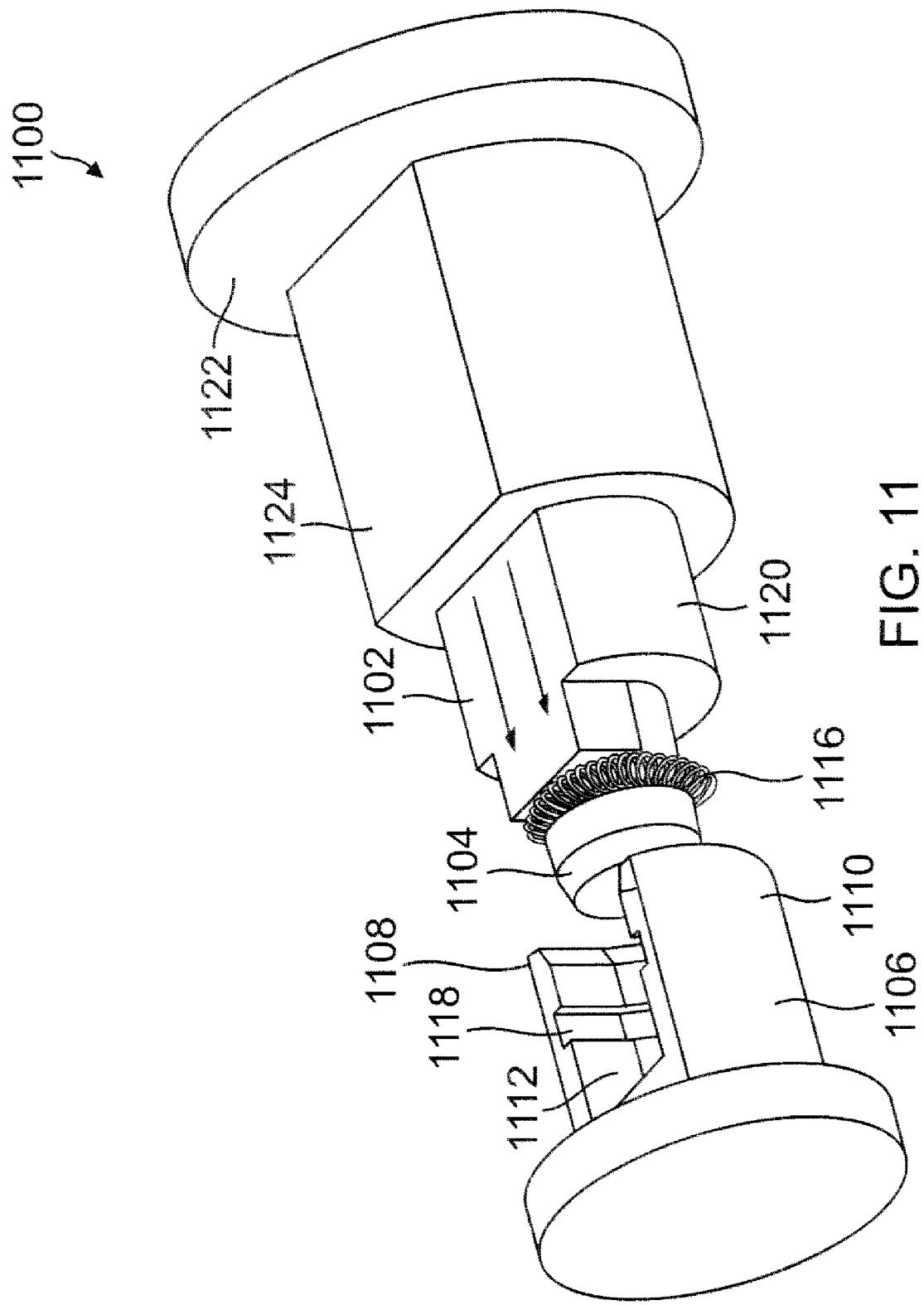

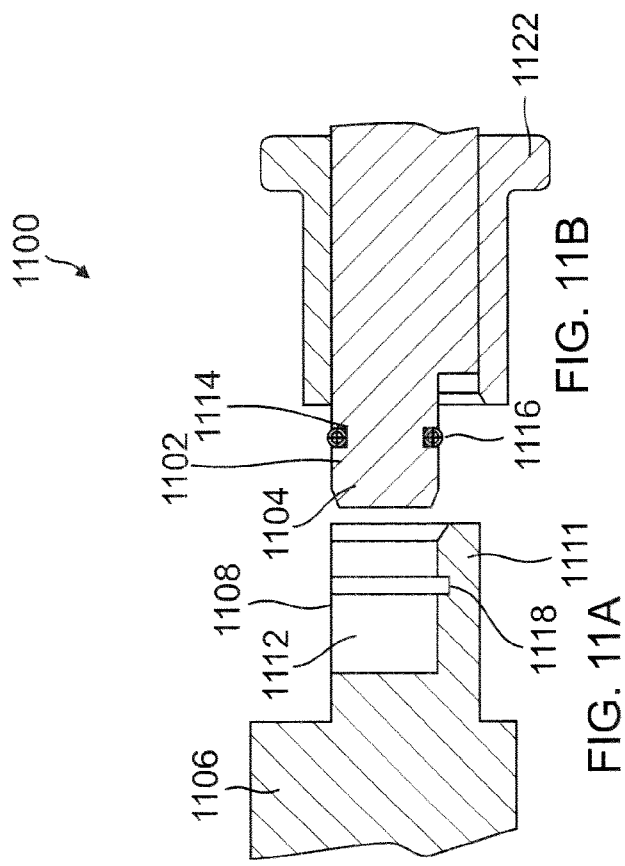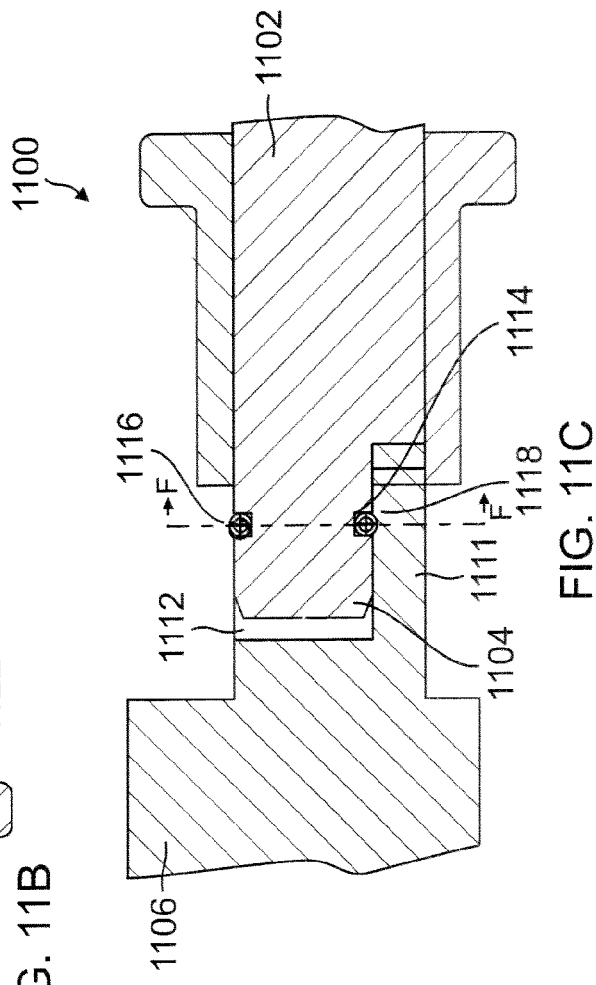

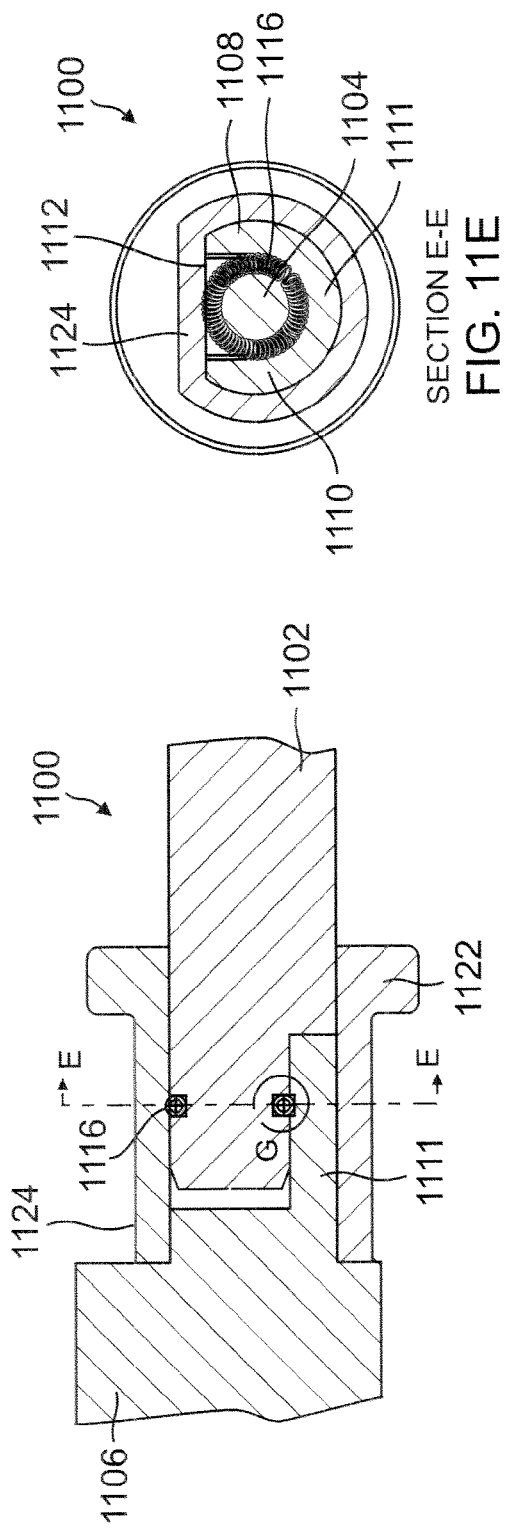
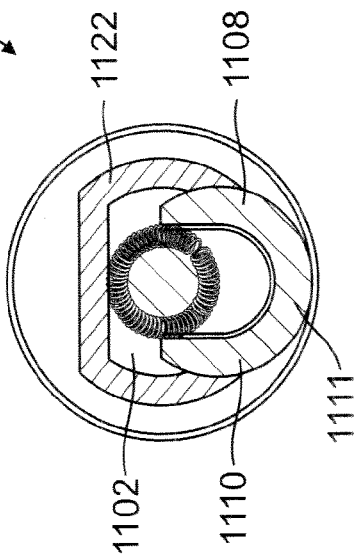
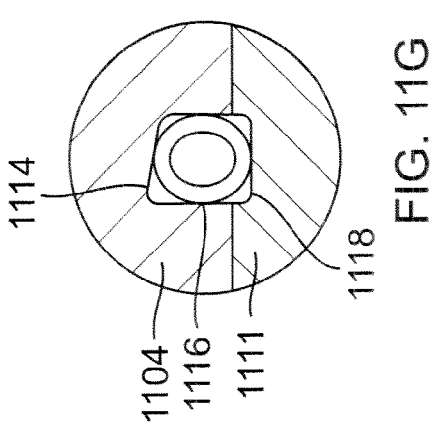

LOCKING MECHANISM WITH QUICK DISASSEMBLY MEANS

CROSS-REFERENCE TO RELATED APPLICATION

This application claims priority to provisional application Ser. No. 61/015,915, filed on Dec. 21, 2007, the entire contents of which are hereby expressly incorporated by reference for all purposes.

BACKGROUND

The orthopedic and laboratory industries, among others, use various tools to perform different functions such as drilling, reaming, scraping, filing, etc. Quick tool interchangeability and very little play between mating tool parts are important considerations in such industries and wherever quick-change connectors are used. At present, different tools can be quickly interchanged by manually removing and replacing a desired interchangeable component of the main base tool, which can universally attach to a variety of interchangeable components by means of a universal clamp or chuck. An example tool utilizing a quick-change connector is a drill where numerous rotary attachments such as reaming or burring attachments can be interchanged by axial removal and insertion.

The present embodiments simplify the method of assembling such tools by providing a rapid means for installing and removing such components. Interchangeable components being incorporated are held in place by individual holders that provide secure axial locking means and quick radial removal means requiring no axial space for the removal of such components from the main base tool. In a typical orthopedic application, for example, interchangeable component holders may be installed in a stationary drill press or a portable drill, depending on the application. The holder is permanently secured to the drilling machine and the interchangeable component can be axially or radially installed, axially locked upon installation but radially removable. In the assembled position, the holder provides circumferential concentricity and the component is axially locked.

The axial locking means may comprise, for example, an axially mounted canted-coil spring, in either the stationary or the rotary portion of the holder combination. In some embodiments, a sleeve restricts radial movement and a non-cylindrical tongue of the interchangeable component and corresponding slot in the holder may allow rotational movement to be transferred between the component and holder. A combination of factors contributes to axial locking motion. The combination may include one or more of:

The groove width is smaller than the coil height so that an interference occurs at assembly between the coil height and the groove width. The interference may range from no interference to approximately 25%, but is preferably between about 5-10% of the coil height so that the spring is firmly retained in the cavity, while at the same time allowing deflection of the spring along the minor axis during locking.

Interference between the groove height and the coil width along the major axis to reduce or prevent radial movement of the components. Such variation may range from no interference to approximately 15%, but more preferably is under 10%, such as less than 5%.

Deflection of the spring coils during assembly to achieve locking. The deflection may range from about 1% to the maximum safe deflection of the coil. The maximum safe deflection may be about 15-25% deflection along the minor axis, but not exceeding the safe deflection, that can cause permanent deformation of the spring's coils.

Tapered locking angle at the bottom of the groove. The taper may range from zero up to about 30%, but is preferably from approximately 5% to approximately 15% to provide a gradual locking action without achieving permanent deformation of the coil.

Aspects of the present embodiments include a number of different "rotary locking mechanisms with quick radial disassembly means." with each providing certain useful advantages. The embodiments are configured as providing locking between a housing and a piston. In actual application of the embodiments as a mechanism for interchangeable tools, the holder and the interchangeable component(s) can correspond to either the piston and housing or housing and piston respectively in reference to the figures of the designs. Those of ordinary skill in the art will appreciate that the embodiments may be practiced other than as specifically described, and should not be limited to the embodiments described herein.

SUMMARY

The various embodiments of the present locking mechanism with quick disassembly means have several features, no single one of which is solely responsible for their desirable attributes. Without limiting the scope of the present embodiments as expressed by the claims that follow, their more prominent features now will be discussed briefly.

One embodiment of the present locking mechanism for use in quick-release applications comprises a housing including a longitudinal axis. A first end portion of the housing includes first and second furcations defining a slot therebetween. An inner surface of the first furcation includes a first groove therein. The locking mechanism further comprises a piston including a body section. A first end of the body section defines first and second shoulders. A tongue extends away from the shoulders along the longitudinal axis. A surface of the tongue includes a second groove therein. The locking mechanism further comprises a sleeve slidably engaging an outer surface of the piston body section. The locking mechanism further comprises a canted-coil spring. The locking mechanism further comprises a first configuration in which the tongue is disposed within the slot such that the furcations abut the shoulders and the first and second grooves are aligned, the canted-coil spring is disposed within the first and second grooves and is compressed by the first and second grooves, and the sleeve is positioned over at least a portion of a junction between the housing and the piston such that the sleeve engages the outer surface of the piston body section and outer surfaces of the furcations, thereby resisting relative motion of the housing and the piston in a direction perpendicular to the longitudinal axis.

Another embodiment of the present locking mechanism for use in quick-release applications comprises a housing including a longitudinal axis. A first end portion of the housing includes first and second furcations defining a slot therebetween. An inner surface of the first furcation includes a first groove therein. An inner surface of the second furcation includes a second groove therein. The locking mechanism further comprises a piston including a body section. A first end of the body section defines first and second shoulders. A tongue extends away from the shoulders along the longitudinal axis. A surface of the tongue includes a continuous perimeter groove therein. The locking mechanism further comprises a sleeve slidably engaging an outer surface of the piston body section. The locking mechanism further comprises a canted-coil spring disposed within the continuous perimeter groove. The locking mechanism further comprises a first configuration in which the tongue is disposed within the slot such that the furcations abut the shoulders and the continuous perimeter groove is aligned with the first and second grooves, the canted-coil spring is disposed within the first and second grooves and is compressed by the first and second grooves, and the sleeve is positioned over at least a portion of a junction between the housing and the piston such that the sleeve engages the outer surface of the piston body section and outer surfaces of the furcations, thereby preventing relative motion of the housing and the piston in a direction perpendicular to the longitudinal axis.

BRIEF DESCRIPTION OF THE DRAWINGS

The various embodiments of the present locking mechanism now will be discussed in detail with an emphasis on highlighting the advantageous features. These embodiments depict the novel and non-obvious locking mechanism shown in the accompanying drawings, which are for illustrative purposes only. These drawings include the following figures, in which like numerals indicate like parts:

FIG. 1A is a cross-sectional front elevation view of one embodiment of a housing portion of the present locking mechanism;

FIG. 1B is a cross-sectional front elevation view of one embodiment of a piston portion of the present locking mechanism;

FIG. 1C is a cross-sectional front elevation view of the housing portion and the piston portion of FIGS. 1A and 1B in an assembled configuration;

FIG. 1D is a top plan view of the housing portion and the piston portion of FIGS. 1A and 1B in a partially disassembled configuration;

FIG. 1E is a cross-sectional left side elevation view of the housing portion and the piston portion of FIGS. 1A and 1B taken through the line E-E in FIG. 1C;

FIG. 1F is a cross-sectional left side elevation view of the housing portion and the piston portion of FIGS. 1A and 1B taken through the line F-F in FIG. 1D;

FIG. 1G is a detail view of the portion of FIG. 1C indicated by the circle G;

FIG. 1H is a cross-sectional top plan view of the housing portion and the piston portion of FIGS. 1A and 1B taken through the line H-H in FIGS. 1A and 1B;

FIG. 1J is a cross-sectional front elevation view of the housing portion and the piston portion of FIGS. 1A and 1B in an assembled configuration and including an alternative embodiment of the sleeve portion;

FIG. 1L is a detail view of the portion of FIG. 1J indicated by the circle L;

FIG. 3A is a cross-sectional front elevation view of another embodiment of the present locking mechanism in an assembled configuration:

FIG. 3B is a cross-sectional left side elevation view of the housing portion and the piston portion of FIG. 3A taken through the line B-B in FIG. 3A:

FIG. 3C is a detail view of the portion of FIG. 3A indicated by the circle C;

FIG. 3D is a detail cross-sectional bottom plan view of an axial spring portion of FIG. 3A, taken through the line D-D in FIG. 3A;

FIG. 3E is a detail cross-sectional bottom plan view of an axial spring portion of FIG. 3A, taken through the line E-E in FIG. 3A;

FIG. 5A is a cross-sectional front elevation view of another embodiment of the present locking mechanism in an assembled configuration:

FIG. 5B is a cross-sectional left side elevation view of the housing portion and the piston portion of FIG. 5A taken through the line B-B in FIG. 5A:

FIG. 5C is a detail view of the portion of FIG. 5A indicated by the circle C;

FIG. 5D is a detail view of the portion of FIG. 5A indicated by the circle D;

FIG. 6A is a cross-sectional front elevation view of another embodiment of the present locking mechanism in an assembled configuration:

FIG. 6B is a cross-sectional left side elevation view of the housing portion and the piston portion of FIG. 6A taken through the line B-B in FIG. 6A;

FIG. 6C is a detail view of the portion of FIG. 6A indicated by the circle C:

FIG. 6D is a detail view of the portion of FIG. 6A indicated by the circle D:

FIG. 7A is a cross-sectional front elevation view of another embodiment of the present locking mechanism in an assembled configuration;

FIG. 7B is a cross-sectional left side elevation view of the housing portion and the piston portion of FIG. 7A taken through the line B-B in FIG. 7A;

FIG. 7C is a front elevation view of the axially-canted-coil spring of FIG. 7A:

FIG. 8A is a cross-sectional front elevation view of another embodiment of the present locking mechanism in an assembled configuration:

FIG. 8B is a cross-sectional left side elevation view of the housing portion and the piston portion of FIG. 8A taken through the line B-B in FIG. 8A;

FIG. 10 is a front perspective view another embodiment of the present locking mechanism in an assembled configuration;

FIG. 10A is a cross-sectional front elevation view of die housing portion of the locking mechanism of FIG. 10;

FIG. 10B is a cross-sectional front elevation view of the piston portion of the locking mechanism of FIG. 10;

FIG. 10C is a cross-sectional front elevation view of the housing portion and the piston portion of FIGS. 10A and 10B in a partially assembled configuration;

FIG. 10D is a cross-sectional front elevation view of the housing portion and the piston portion of FIGS. 10A and 10B in a fully assembled, configuration;

FIG. 10E is a cross-sectional left side elevation view of the housing portion and the piston portion of FIG. 10D taken through the line E-E in FIG. 10D;

FIG. 10F is a cross-sectional left side elevation view of the housing portion and the piston portion of FIG. 10C taken through the line F-F in FIG. 10C;

FIG. 10G is a detail view of the portion of FIG. 10D indicated by the circle G;

FIG. 11 is a front perspective view another embodiment of the present locking mechanism in an assembled configuration;

FIG. 11A is a cross-sectional front elevation view of the housing portion of the locking mechanism of FIG. 11;

FIG. 11B is a cross-sectional front elevation view of the piston portion of the locking mechanism of FIG. 11;

FIG. 11C is a cross-sectional front elevation view of the housing portion and the piston portion of FIGS. 11A and 11B in a partially assembled configuration;

FIG. 11D is a cross-sectional front elevation view of the housing portion and the piston portion of FIGS. 11A and 11B in a fully assembled configuration;

FIG. 11E is a cross-sectional left side elevation view of the housing portion and the piston portion of FIG. 11D taken through the line E-E in FIG. 11D;

FIG. 11F is a cross-sectional left side elevation view of the housing portion and the piston portion of FIG. 11C taken through the line F-F in FIG. 11C; and FIG. 11G is a detail view of the portion of FIG. 11D indicated by the circle G.

DETAILED DESCRIPTION

The detailed description set forth below in connection with the appended drawings is intended as a description of the presently preferred embodiments of a simple release locking mechanism and is not intended to represent the only forms in which the present embodiments may be constructed or used. The description sets forth the features and the steps for constructing and using the simple release locking mechanism of the present embodiments. It is to be understood, however, that the same or equivalent functions and structures may be accomplished by different embodiments that are also intended to be encompassed within the spirit and scope of the embodiments. As denoted elsewhere herein, like element numbers are intended to indicate like or similar elements or features.

Unless specifically noted, it is intended that the words and phrases in the specification and the claims be given their ordinary and accustomed meaning to those of ordinary skill in the applicable arts. If any other special meaning is intended for any word or phrase, the specification will clearly state and define the special meaning. In particular, most words have a generic meaning. If it is intended to limit or otherwise narrow the generic meaning, specific descriptive adjectives will be used to do so. Absent the use of special adjectives, it is intended that the terms in this specification and claims be given their broadest possible, generic meaning. For example, unless the context indicates otherwise, a canted-coil spring can be either an axial or a radial canted-coil spring. It can also be a hybrid, with characteristics of both axial and radial springs. It can also have different configurations, such as round, oval, square, etc.

The illustrated embodiments of the present locking mechanism discussed herein include canted coil springs. In certain embodiments the coil springs may be radially canted, while in certain other embodiments the coil springs may be axially canted. In still further embodiments the coil springs may be both radially canted and axially canted. Canted coil springs are described in detail in U.S. Pat. Nos. 4,655,462; 4,826,144; 4,876,781; 4,907,788; 4,915,366; 4,964,204; 5,139,243; 5,160,122; 5,503,375; 5,615,870; 5,709,371; 5,791,638; and 7,055,812. The contents of each of the foregoing patents are hereby incorporated by reference herein.

Figure 1M:
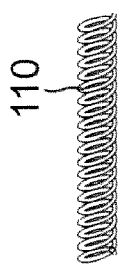
FIG. 1M is a front elevation view of the axially-canted-coil spring FIG. 1A.

FIGS. 1A-1H and 1J-1M illustrate one embodiment of the present locking mechanism 100. With reference to FIGS. 1A and 1B, the locking mechanism 100 includes a generally cylindrical housing 101 having a longitudinal axis 103. The housing 101 comprises a first furcation 102 and a second furcation 104 in a first end portion. The first and second furcations 102, 104 define a slot 106 therebetween. The slot 106 is an open space that is shaped substantially as a rectangular parallelepiped, being bounded along three faces by the housing 101 and the furcations 102, 104, and being open along the remaining three faces. Those of ordinary skill in the art will appreciate that in alternative embodiments the slot 106 may have other configurations. With reference to FIGS. 1A and 1H, an inner surface 107 of the first furcation 102 includes a taper bottom groove 108 that retains a linear axially-canted-coil spring 110. The spring length runs perpendicular to the longitudinal axis 103. The linear canted-coil spring 110 is illustrated in further detail in FIG. 1M. In other embodiments, the tapered bottom groove may be located on the second furcation 104.

The locking mechanism 100 further includes a generally cylindrical piston 112 configured to assemble in-line with the housing 101. The piston 112 includes a body section 114 and a longitudinal axis 103. A piston tongue 116 extends away from the body section 114, defining first and second shoulders 118 to either side of the tongue 116. In the illustrated embodiment, the tongue 116 is shaped substantially as a rectangular parallelepiped. However, with reference to FIG. 1E, two opposite faces of the tongue 116 are convex so that when the tongue 116 is disposed in the slot 106 an outer surface of the slot 106/tongue 116 junction is substantially cylindrical. Those of ordinary skill in the art will appreciate that in alternative embodiments the tongue 116 may have other shapes.

With reference to FIGS. 1A and 1B, a first face 120 of the tongue 116 includes a flat bottomed groove 122. The groove 122 receives the linear canted-coil spring 110 when the locking mechanism 100 is in the assembled configuration of FIG. 1C. The groove 122 contributes to the locking action in the locking mechanism 100, as explained in further detail below.

With continued reference to FIGS. 1A and 1B, the outer surface 124 of the piston 112 includes a circumferential groove 126. The circumferential groove 126 receives a circular or garter radially-canted-coil spring 128. The circular radially-canted-coil spring 128 is illustrated in greater detail in FIG. 1N.

In one embodiment, the circular canted-coil spring 128 may be secured inside the circumferential groove 126 by controlling a spring squeeze between the groove 126 and the spring 128. In alternative embodiments, or in the event the spring 128 does not have enough squeeze, the ends of the groove 126 could be pinned or staked such as to cap the channel of the groove to retain the spring 128 therein.

A generally cylindrical sleeve 130 is mounted over the outer surface 124 of the piston 112. The sleeve 130 is slidable along the outer surface 124 between the retracted position, of FIG. 1B and the closed position of 1C. In the retracted position the sleeve 130 is spaced apart from the circular canted-coil spring 128 on a side of the spring 128 opposite the tongue 116. In the closed position the sleeve 130 covers the spring 128 to retain the housing 101 and the piston 112 in the assembled configuration, as described in further detail below.

To assemble the illustrated locking mechanism 100, the tongue 116 is inserted into the slot 106 as illustrated in FIG. 1C. The tongue 116 may be inserted into the slot 106 by relative axial movement of the housing 101 and the piston 112, as shown by the arrow 132 in FIGS. 1A, 1B and 1H. The tongue 116 is inserted into the slot 106 until the ends of the furcations 102, 104 contact the shoulders 118. In this configuration the groove 122 in the tongue 116 at least partially aligns with the groove 108 in the inner surface 107 of the first furcation 102. The linear canted-coil spring 110 is thus compressed between the two grooves 108, 122 as shown in the detail view of FIG. 1G. The compressed spring 110 provides locking action that prevents the axial separation of the housing 101 and the piston 112, as described in further detail, below.

FIG. 1G shows the manner in which the axial locking occurs. First, the groove width (G.W.) is smaller than the coil height (C.H.). Second, a base 134 of the groove 108 is tapered such that a depth of the groove increases with increasing distance from a second end portion 136 (FIG. 1C) of the housing 101. The taper bottom groove 108 facilitates the counter-clockwise rotation of the linear canted-coil spring 110 as the tongue 116 is inserted axially into the slot 106. Further the relative dimensions of groove width and coil height in combination with the taper bottom groove also retards the reverse rotation of the coil spring 110 as the tongue 116 is withdrawn axially from the slot 106, as occurs when a tensile force is applied to the locking mechanism 100. Consequently, a greater force is required to remove the tongue 116 axially from the slot 106 than is required to insert the tongue 116 axially into the slot 106. The magnitude of the difference between the insertion force and the removal, force can be adjusted by adjusting the relative dimensions of groove width and coil height and the angle 144 of the taper bottom groove 108. In certain embodiments the angle 144 of the taper bottom groove 108 may be tapered to produce a spring in a convex initial position. In other embodiments, the angle produces a spring in a concave initial position. In still other embodiments the magnitude of the removal force may be so great that the tongue 116 cannot be removed axially from the slot 106 without destroying the spring 110. These concepts are described in detail in U.S. Pat. Nos. 4,678,210; 5,082,390; 5,411,348; 5,545,842; 6,749,358; 6,835,084; 7,055,812, 7,070,455 and 7,195,523, all of which are incorporated herein by reference.

To complete the assembly of the locking mechanism, the sleeve 130 is slid along the piston 112 from the retracted position of FIG. 1B to the closed position of 1C. In the closed position an end 138 of the sleeve 130 abuts a shoulder 140 on the housing 101 to prevent further movement of the sleeve 130 toward the housing 101. In the closed position the sleeve 130 covers the spring 128 and compresses the spring 128 into the circumferential groove 126, Friction between the spring 128 and the sleeve 130 thus resists sliding movement of the sleeve 130 away from the housing 101. The inner surface of the sleeve 130, however, is smooth. Thus, the sleeve 130 is not locked against sliding movement relative to the piston 112. Rather, sliding movement relative to the piston 112 is merely retarded by the friction between the spring 128 and the sleeve 130. In the closed position the sleeve 130 also covers the junction between the tongue 116 and the slot 106. In inner surface of the sleeve 130 contacts the outer surfaces of the furcations 102, 104 and the tongue 116, as illustrated in the cross-sectional view of FIG. 1E. The sleeve 130 thus prevents relative movement of the housing 101 and the piston 112 in a direction perpendicular to the longitudinal axis 103. In the assembled configuration, the housing 101 and the piston 112 are thus locked because they cannot be separated from one another in either the axial direction (parallel to the longitudinal axis 103) or the radial direction (perpendicular to the longitudinal axis 103).

With reference to FIGS. 1A, 1B, 1C and 1G, it is possible to insert the tongue 116 into the slot 106 in a configuration in which the piston 112 is rotated 180° about its longitudinal axis from the configuration shown in FIG. 1C. In this reversed configuration, locking action may not occur between the housing 101 and the piston 112 because the groove 122 in the tongue 116 would not align with the groove 108 in the slot 106. Therefore, in order to ensure locking action the piston 112 is preferably inserted into the housing 101 in the orientation shown in FIGS. 1A-1C in which the grooves 108, 122 line up. In one example embodiment, a longitudinally aligned combination tongue-and-group is incorporated for alignment purposes, which would run parallel to but offset from the longitudinal axis of the piston, instead of the current orthogonal configuration to the longitudinal axis of the piston. In alternative embodiments, external markers may be provided as alignment indicia.

FIGS. 1D and 1F illustrate a method of disassembling the housing 101 and the piston. 112 from one another. The reader will note that the cross-sectional view of FIG. 1F is taken through the line F-F in FIG. 1D, but FIG. 1F has been rotated 90° counter-clockwise from the orientation shown in FIG. 1D. To disassemble the housing 101 and the piston 112 from, one another, first the sleeve 130 is slid along the piston 112 from the closed position (FIG. 1C) to the retracted position (FIG. 1D). Next, the housing 101 and the piston 112 are moved relative to one another in the radial direction (perpendicular to the longitudinal axis 103, as indicated by the arrows 142 in FIGS. 1D and 1F). The compressed linear spring 110 resists, but does not prevent, relative sliding movement of the housing 101 and the piston 112. These components can thus be separated from one another by relative radial movement once the locking sleeve 130 is moved to the retracted position.

Figure 1K:
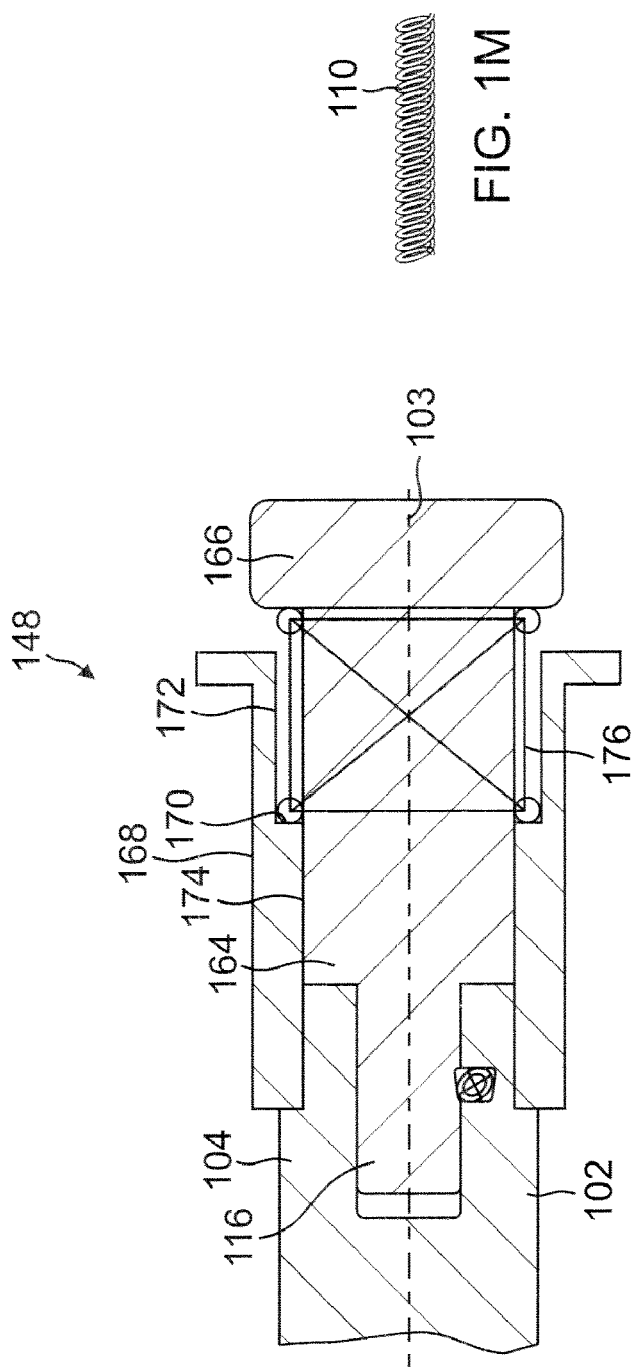
FIG. 1K is a cross-sectional front elevation view of the housing portion and the piston portion of FIGS. 1A and 1B in an assembled configuration and including an alternative embodiment of the sleeve portion.
Figure 1N:
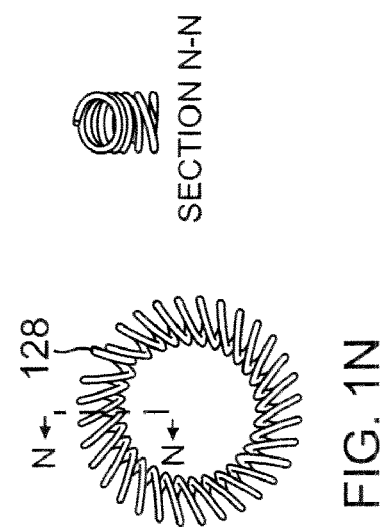
FIG. 1N is a front elevation view of the radially-canted-coil spring FIG. 1A.

FIGS. 1J, 1K, and 1L illustrate alternate configurations for the present locking mechanism 146, 148. With reference to FIGS. 1J and 1L, in the illustrated embodiment 146 the sleeve 150 includes a circumferential groove 152 on its inner surface. When the sleeve 150 is slid to the locked position (FIG. 1J), the groove 152 at least partially aligns with a circumferential taper bottom groove 154 in the piston 156. The groove 152 thus receives an axially canted-coil spring 158 and compresses the axially canted-coil spring 158 between the groove 152 and the groove 154. The compressed spring 158 resists, but does not prevent the sleeve 150 from sliding away from the housing 101 and out of the locked position. In contrast to the taper bottom groove 108 illustrated in FIG. 1G, the taper bottom groove 154 tapers in the opposite direction. Thus, as the sleeve 150 slides to the right relative to the piston 156 in FIG. 1L, the sleeve 150 moves across the groove 154 from its deep end 160 toward its shallow end 162. There is thus room for the spring 158 to rotate clockwise under the influence of friction from the groove 152 and the inner surface of the sleeve 150.

FIG. 1K illustrates another embodiment 148 in which the piston 164 does not include a circumferential groove retaining a circular coil spring. Instead, the piston 164 includes an end portion 166 having an enlarged outer diameter. The sleeve 168 includes an annular shoulder 170 formed at a junction between a first inner diameter portion 172 and a second inner diameter portion 174. A coil spring 176 (or similar resilient member) is held in compression between the enlarged end portion 166 and the annular shoulder 170. The compressive force in the spring 176 holds the sleeve 168 in the closed position in which it covers the junction between the furcations 102, 104 and the tongue 116. An operator may squeeze the sleeve 168 with his hand (or with a tool) to slide the sleeve 168 along the piston 164 toward the enlarged end portion 166 until it no longer covers the junction between the furcations 102, 104 and the tongue 116. With the sleeve 168 no longer covering the junction, the housing 101 and piston 164 may be separated by relative movement in the radial direction (perpendicular to the longitudinal axis 103).

Figure 2B:
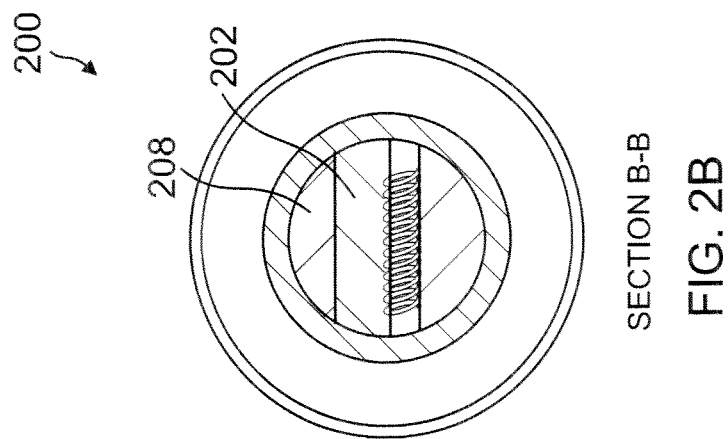
FIG. 2B is a cross-sectional left side elevation view of the housing portion and the piston portion of FIG. 2A taken through the line B-B in FIG. 2A.
Figure 2A:
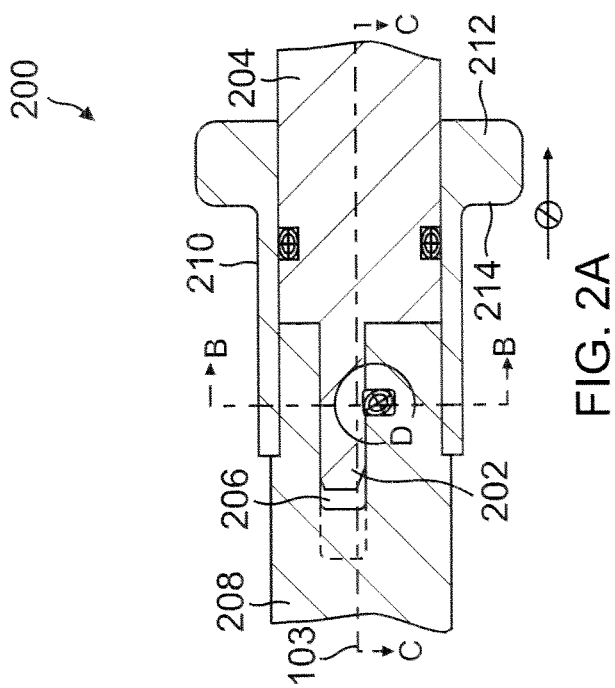
FIG. 2A is a cross-sectional front elevation view of another embodiment of the present locking mechanism in an assembled configuration.
Figure 2C:
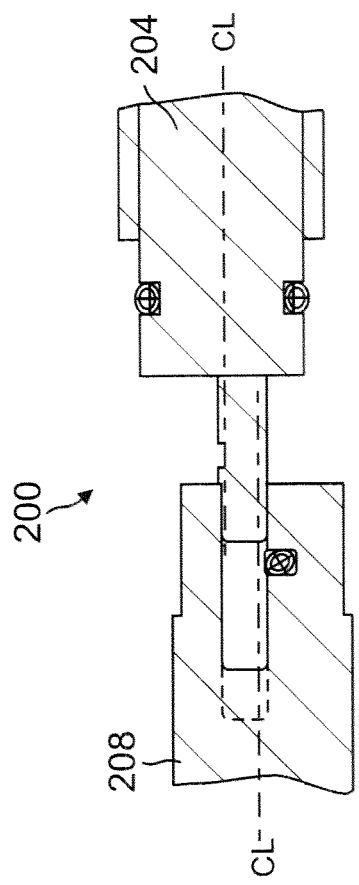
FIG. 2C is a cross-sectional front elevation view of the locking mechanism of FIG. 2A in an improperly assembled configuration.

FIGS. 2A-2C illustrate another embodiment of the present locking mechanism 200. The locking mechanism 200 includes many of the same features described above with respect to the locking mechanism 100 illustrated in FIGS. 1A-1H and 1J-1M. Accordingly, the discussion below will focus on only the differences between the embodiments. With reference to FIG. 2A, in the locking mechanism 200 the tongue 202 of the piston 204 is offset from the longitudinal axis 103. The slot 206 of the housing 208 is similarly offset from the longitudinal axis 103. The offset of the tongue 202 and the slot 206 contribute to proper alignment of the housing 208 and the piston 204. If the housing 208 and the piston 204 are misaligned, as shown in FIG. 1C, the misalignment will be obvious to the operator.

In the locking mechanism 200 the sleeve 210 includes an enlarged end portion 212 spaced from the housing 208. The enlarged end portion 212 provides a bearing surface 214 for the operator's hand or a tool, facilitating the sliding movement of the sleeve 210 aware from the closed position of FIG. 2A.

FIGS. 3A-3E illustrate another embodiment of the present locking mechanism 300. The locking mechanism 300 includes many of the same features described above with respect to the locking mechanisms 100, 200 illustrated in FIGS. 1A-1H, 1J-1M and 2A-2C. Accordingly, the discussion below will focus on only the differences between the embodiments. With reference to FIGS. 3A-3D, in the locking mechanism 300 a first surface 301 the tongue 302 of the piston 304 includes a taper bottom groove 306 chat retains a linear axially-canted-coil spring 308. A first surface 310 of the first furcation 312 of the housing 314 includes a flat bottomed groove 316. Accordingly, with reference to FIGS. 1G and 3C the configuration of the grooves 306, 316 in the locking mechanism 300 is the reverse of the configuration of the grooves 108, 122 in the locking mechanism 100. However, the function of the grooves 306, 316 is identical to the function of the grooves 108, 122, which is described in detail above and will not be repeated here. With reference to FIGS. 3D and 3E, the taper bottom groove 306 may extend perpendicular to the longitudinal axis 103 (FIG. 3D), or it may lie at a non-perpendicular to the longitudinal axis 103 (FIG. 3E). The linear canted-coil spring 308 assumes the same angle to the longitudinal axis 103 as the groove 306. Those of ordinary skill in the art will appreciate that the illustrated angles for the taper bottom groove 306 and linear canted-coil spring 308 are applicable to all of the present embodiments, regardless of whether they are specifically discussed with respect to any particular embodiment.

Figure 4:
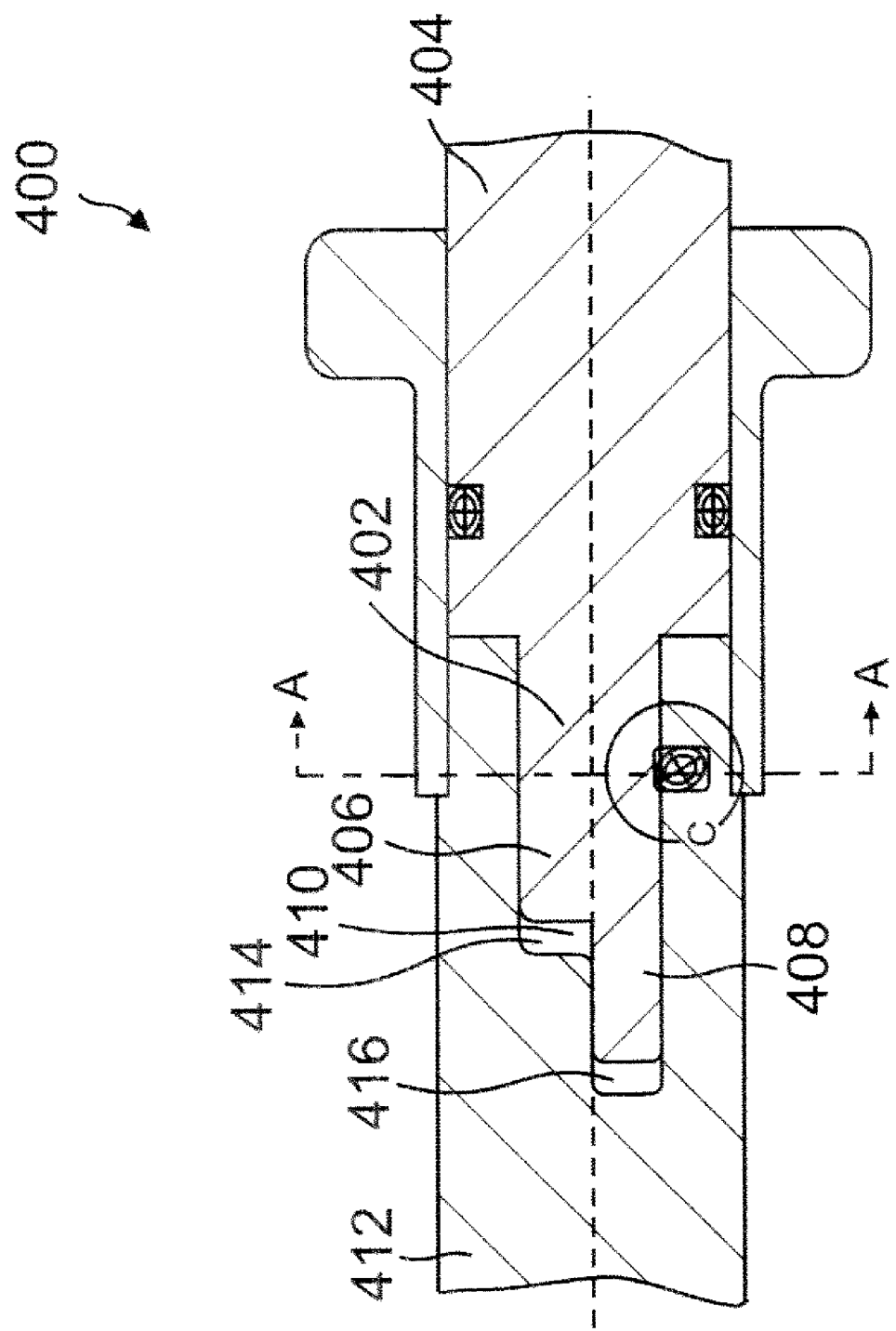
FIG. 4 is a cross-sectional front elevation view of another embodiment of the present locking mechanism in an assembled configuration.

FIG. 4 illustrates another embodiment of the present locking mechanism 400. The locking mechanism 400 includes many of the same features described above with respect to the locking mechanisms 100, 200, 300 illustrated in FIGS. 1A-1H, 1J-1M, 2A-2C and 3A-3E. Accordingly, the discussion below will focus on only the differences between the embodiments. With reference to FIG. 4, in the locking mechanism 400 the tongue 402 of the piston 404 includes a step defined by a first portion 406 having a relatively shorter length and a second portion 408 having a relatively longer length. The slot 410 in the housing 412 similarly includes a step defined by a first portion 414 having a relatively lesser depth and a second portion 416 having a relatively greater depth. The steps contribute to proper alignment of the housing 412 and the piston 404. The tongue 402 may only be inserted completely within the slot 410 when the tongue first portion 406 is aligned with the slot first portion 414 and the tongue second portion 408 is aligned with the slot second portion 416. If the housing 412 and the piston 404 are misaligned, the misalignment will be obvious to the operator.

FIGS. 5A-5D illustrate another embodiment of the present locking mechanism 500. The locking mechanism 500 includes many of the same features described above with respect to the locking mechanisms 100, 200, 300, 400 illustrated in FIGS. 1A-1H, 1J-1M, 2A-2C, 3A-3E and 4. Accordingly, the discussion below will focus on only the differences between the embodiments. With reference to FIGS. 5A, 5B and 5D, in the locking mechanism 500 a first surface 502 of the first furcation 504 of the housing 506 includes a taper bottom groove 508 that retains a linear axially-canted-coil spring 510. A first surface 512 of the tongue 514 of the piston 516 includes a flat bottomed groove 518. With reference to FIGS. 5A-5C, in the locking mechanism 500 a first surface 520 of the second furcation 522 of the housing 506 includes a taper bottom, groove 524 that retains a linear canted-coil spring 510. A second surface 526 of the tongue 514 of the piston 516 includes a flat bottomed groove 528. The function of the grooves 508, 518, 524, 528 is identical to the function of the grooves 108, 122, which is described in detail above and will not be repeated here. However, because the locking mechanism 500 includes two linear canted-coil springs 510 and associated grooves, in certain embodiments it may provide greater axial holding power than the locking mechanisms including only one linear canted-coil spring and associated grooves.

FIGS. 6A-6D illustrate another embodiment of the present locking mechanism 600. The locking mechanism 600 includes many of the same features described above with respect to the locking mechanisms 100, 200, 300, 400, 500 illustrated in FIGS. 1A-1H, 1J-1M 2A-2C, 3A-3E, 4 and 5A-5D. Accordingly, the discussion below will focus on only the differences between the embodiments. With reference to FIGS. 6A-6C, in the locking mechanism 600 a first surface 602 of the tongue 604 of the piston 606 includes a taper bottom groove 608 that retains a linear axially-canted-coil spring 610. A first surface 612 of the first furcation 614 of the housing 616 includes a fiat bottomed groove 618. With reference to FIGS. 6A, 6B and 6D, in the locking mechanism 600 a second surface 620 of the tongue 604 of the housing 606 includes a taper bottom groove 622 that retains a linear canted-coil spring 610. A first surface 624 of the second furcation 626 of the piston 616 includes a flat bottomed groove 628. The function of the grooves 608, 618, 622, 628 is identical to the function of the grooves 306, 316, which is described in detail above and will not be repeated here. However, because the locking mechanism 600 includes two linear canted-coil springs 610 and associated grooves, in certain, embodiments it may provide greater axial holding power than the locking mechanisms including only one linear canted-coil spring and associated grooves.

FIGS. 7A-7C illustrate another embodiment of the present locking mechanism 700. The locking mechanism 700 includes many of the same features described above with respect to the locking mechanisms 100, 200, 300, 400, 500, 600 illustrated in FIGS. 1A-1H, 1J-1M, 2A-2C, 3A-3E, 4, 5A-5D and 6A-6D. Accordingly, the discussion below will focus on only the differences between the embodiments. With reference to FIGS. 7A and 7B, the locking mechanism 700 includes a piston 702 having a tongue 704. With reference to FIG. 7B, the tongue 704 has a square cross-section. The locking mechanism 700 further includes a housing 706 having a first furcation 708 and a second furcation 710. A slot 712 defined between the first and second furcations 708, 710 is sized and configured to receive the square tongue 704 in locking engagement.

With continued reference to FIGS. 7A and 7B, the square tongue 704 includes a circumferential taper bottom groove 714 that extends around all four outer faces of the square tongue 704. The circumferential taper bottom groove 714 receives and retains a circular, axially-canted-coil spring 716. The circular, axially-canted-coil spring 716 is illustrated in greater detail in FIG. 7C.

With reference to FIG. 7A, inner surfaces 717 of the first and second furcations 708, 710 each include a respective flat bottom groove 718. Thus, when the square tongue 704 is inserted into the slot 712 as shown in FIG. 7A, the circular, axially-canted-coil spring 716 is compressed along two portions of its length. Those portions are the first portion 720 (FIG. 7B) that lies between a first one of the flat bottom grooves 718 and a first length of the circumferential, taper bottom groove 714 and the second portion 722 (FIG. 7B) that lies between a second one of the flat bottom grooves 718 and a second length of the circumferential taper bottom groove 714. The interaction of the grooves 714, 718 and the compressed spring portions 720, 722 prevents the axial separation of the housing 706 and the piston 702 in the same manner as described above with respect to the previous embodiments. The housing 706 and the piston 702 may be separated by relative radial movement as also described above with respect to the previous embodiments.

FIGS. 8A-8B illustrate another embodiment of the present locking mechanism 800. The locking mechanism 800 includes many of the same features described above with respect to the locking mechanisms 100, 200, 300, 400, 500, 600, 700 illustrated in FIGS. 1A-1H, 1J-1M, 2A-2C, 3A-3E, 4, 5A-5D, 6A-6D and 7A-7C. Accordingly, the discussion below will focus on only the differences between the embodiments. With reference to FIGS. 8A and 8B, the locking mechanism 800 includes a piston 802 having a tongue 804. With reference to FIG. 8B, the tongue 804 has an oval cross-section comprising opposite flat sections 803 and opposite arcuate sections 805. The locking mechanism 800 further includes a housing 806 having a first furcation 808 and a second furcation 810. A slot 812 defined between the first and second furcations 808, 810 is sized and configured to receive the oval tongue 804 in locking engagement in which the opposite flat sections 803 engage inner surfaces 817 of the first and second furcations 808, 810.

With continued reference to FIGS. 8A and 8B, the oval tongue 804 includes a circumferential taper bottom groove 814 that extends around the opposite flat sections 803 and the opposite arcuate sections 805. The circumferential taper bottom groove 814 receives and retains a circular, axially-canted-coil spring 816.

With reference to FIG. 8A, the first and second furcations 808, 810 each include a respective flat bottom groove 818. Thus, when the oval tongue 804 is inserted into the slot 812 as shown in FIG. 8A, the circular, axially-canted-coil spring 816 is compressed along two portions of its length. Those portions are the first portion 820 (FIG. 8B) that lies between a first one of the flat bottom grooves 818 and a first length of the circumferential taper bottom groove 814 and the second portion 822 (FIG. 8B) that lies between a second one of the flat bottom grooves 818 and a second length of the circumferential taper bottom groove 814. The interaction of the grooves 814, 818 and the compressed spring portions 820, 822 prevents the axial separation of the housing 806 and the piston 802 in the same manner as described above with respect to the previous embodiments. The housing 806 and the piston 802 may be separated by relative radial movement as also described above with respect to the previous embodiments.

Figure 9B:
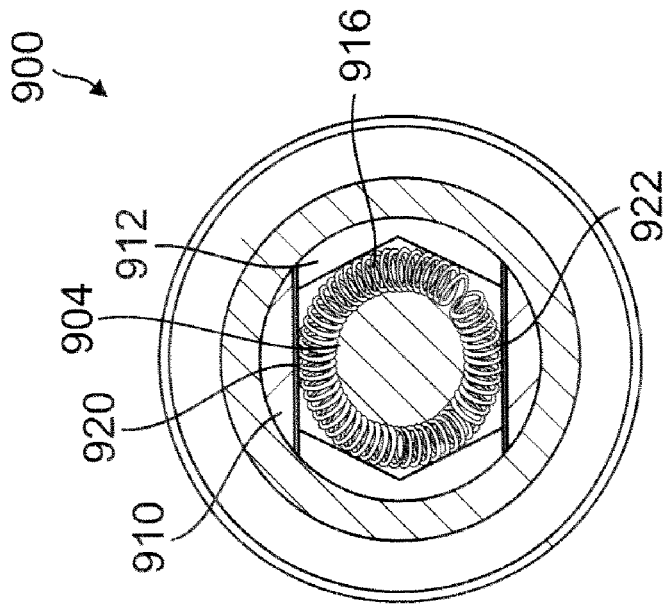
FIG. 9B is a cross-sectional left side elevation view of the housing portion and the piston portion of FIG. 9A taken through the line B-B in FIG. 9A.
Figure 9A:
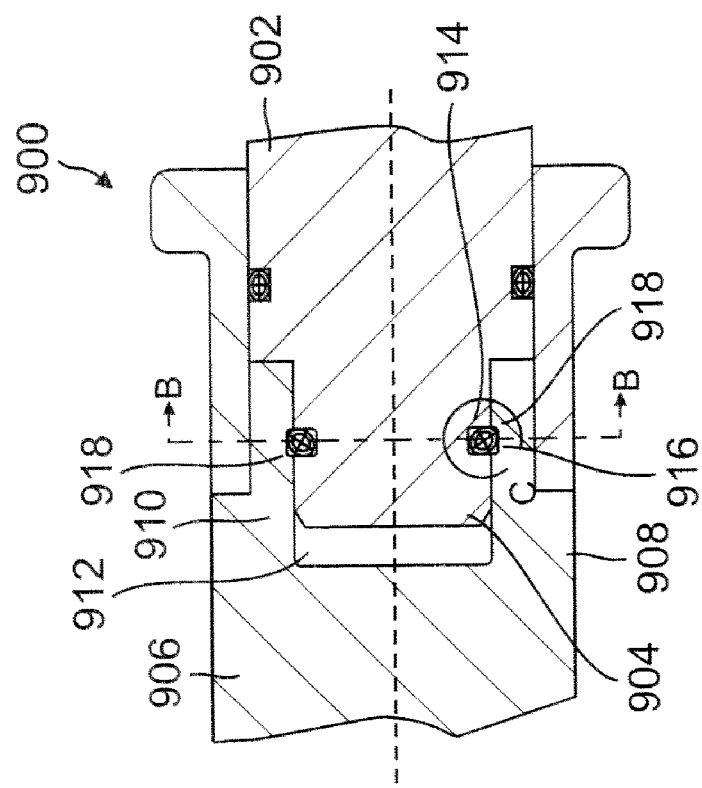
FIG. 9A is a cross-sectional front elevation view of another embodiment of the present locking mechanism in an assembled configuration.

FIGS. 9A-9B illustrate another embodiment of the present locking mechanism 900. The locking mechanism 900 includes many of the same features described above with respect to the locking mechanisms 100, 200, 300, 400, 500, 600, 700, 800 illustrated in FIGS. 1A-1H, 1J-1M, 2A-2C, 3A-3E, 4, 5A-5D, 6A-6D, 7A-7C and 8A-8B. Accordingly, the discussion below will focus on only the differences between the embodiments. With reference to FIGS. 9A and 9B, the locking mechanism 900 includes a piston 902 having a tongue 904. With reference to FIG. 9B, the tongue 904 has a round cross-section. The locking mechanism 900 further includes a housing 906 having a first furcation 908 and a second furcation 910. A slot 912 defined between the first and second furcations 908, 910 is sized and configured to receive the round tongue 904 in locking engagement.

With continued reference to FIGS. 9A and 9B, the round tongue 904 includes a circumferential taper bottom groove 914. The circumferential taper bottom groove 914 receives and retains a circular, axially-canted-coil spring 916.

With reference to FIG. 9A, the first and second furcations 908, 910 each include a respective flat bottom groove 918. Thus, when the round tongue 904 is inserted into the slot 912 as shown in FIG. 9A, the circular, axially-canted-coil spring 916 is compressed along two portions of its length. Those portions are the first portion 920 (FIG. 9B) that lies between a first one of the flat bottom grooves 918 and a first length of the circumferential taper bottom groove 914 and the second portion 922 (FIG. 9B) that lies between a second one of the flat bottom grooves 918 and a second length of the circumferential taper bottom groove 914. The interaction of the grooves 914, 918 and the compressed spring portions 920, 922 prevents the axial separation of the housing 906 and the piston 902 in the same manner as described above with respect to the previous embodiments. The housing 906 and the piston 902 may be separated by relative radial movement as also described above with respect to the previous embodiments.

FIGS. 10-10G illustrate another embodiment of the present locking mechanism 1000. The locking mechanism 1000 includes many of the same features described above with respect to the locking mechanisms 100, 200, 300, 400, 500, 600, 700, 800, 900 illustrated in FIGS. 1A-1H, 1J-1M, 2A-2C, 3A-3E, 4, 5A-5D, 6A-6D, 7A-7C, 8A-8B and 9A-9B. Accordingly, the discussion below will focus on only the differences between the embodiments. With reference to FIGS. 10-10B, the locking mechanism 1000 includes a piston 1002 having a tongue 1004. With reference to FIG. 10E, the tongue 1004 has a round cross-section. The locking mechanism 1000 further includes a housing 1006 having a first furcation 1008 and a second furcation 1010 (FIGS. 10 and 10E). A wall portion 1011 extends between the first and second furcations 1008, 1010 to form a substantially U-shaped cross-section. A slot 1012 bounded by the furcations 1008, 1010 and the wall portion 1011 is sized and configured to receive the round tongue 1004 in locking engagement.

With reference to FIGS. 10B and 10C, the round tongue 1004 includes a circumferential taper bottom groove 1014. The circumferential taper bottom groove 1014 receives and retains a circular, axially-canted-coil spring 1016.

With reference to FIG. 10A, the first and second furcations 1008, 1010 and the wall portion 1011 include a flat bottom groove 1018. Thus, when the round tongue 1004 is inserted, into the slot 1012 as shown in FIGS. 10C and 10D, the circular, axially-canted-coil spring 1016 is compressed along approximately half its length in the areas that abut the groove 1018 in the first and second furcations 1008, 1010 and the wall portion 1011 (FIG. 10E). The interaction of the grooves 1014, 1018 and the compressed spring 1016 prevents the axial separation of the housing 1006 and the piston 1002 in the same manner as described above with respect to the previous embodiments. The housing 1006 and the piston 1002 may be separated by relative radial movement as also described above with respect to the previous embodiments and as shown in FIG. 10F.

FIGS. 11-11G illustrate another embodiment of the present locking mechanism 1100. The locking mechanism 1100 includes many of the same features described above with respect to the locking mechanisms 100, 200, 300, 400, 500, 600, 700, 800, 900, 1000 illustrated in FIGS. 1A-1H, 1J-1M, 2A-2C, 3A-3E, 4, 5A-5D, 6A-6D, 7A-7C, 8A-8B, 9A-9B and 10-10G. Accordingly, the discussion below will focus on only the differences between the embodiments. With reference to FIGS. 11-11B, the locking mechanism 1100 includes a piston 1102 having a tongue 1104. With reference to FIG. 11E, the tongue 1104 has a round cross-section. The locking mechanism 1100 further includes a housing 1106 having a first furcation 1108 and a second furcation 1110 (FIGS. 11 and 11E). A wall portion 1111 extends between the first and second furcations 1108, 1110 to form a substantially U-shaped cross-section. A slot 1112 bounded by the furcations 1108, 1110 and the wall portion 1111 is sized and configured to receive the round tongue 1104 in locking engagement.

With reference to FIGS. 11B and 11C, the round tongue 1104 includes a circumferential taper bottom groove 1114. The circumferential taper bottom groove 1114 receives and retains a circular, axially-canted-coil spring 1116.

With reference to FIG. 11A, the first and second furcations 1108, 1110 and the wall portion 1111 include a flat bottom groove 1118. Thus, when the round tongue 1104 is inserted into the slot 1112 as shown in FIGS. 11C and 11D, the circular, axially-canted-coil spring 1116 is compressed along approximately half its length in the areas that abut the groove 1118 in the first and second furcations 1108, 1110 and the wall portion 1111 (FIG. 11E). The interaction of the grooves 1114, 1118 and the compressed spring 1116 prevents the axial separation of the housing 1106 and the piston 1102 in the same manner as described above with respect to the previous embodiments. The housing 1106 and the piston 1102 may be separated by relative radial movement as also described above with respect to the previous embodiments and as shown in FIG. 11F.

Unlike the previous embodiments, the locking mechanism 1100 does not include a circumferential groove in the body portion 1120 (FIG. 10) of the piston 1102. However, the locking mechanism 1100 includes a sleeve 1122 shaped substantially as a cylinder having a flat side wall 1124. With reference to FIGS. 11D and 11E, when the sleeve 1122 is slid toward the housing 1106 into the locked position, the flat side wall 1124 compresses a portion of the spring 1116 into the circumferential groove 1118. Friction between the spring 1116 and the inner surface of the flat side wall 1124 resists sliding movement of the sleeve 1122 away from the locked position.

In certain aspects of the present embodiments, the housing is part of a rotating or reciprocating shaft of equipment or an appliance, such as a drill or a food mixer, and the piston is part of a removable component, such as a chuck. In another embodiment, the piston is part of a rotating or reciprocating shaft of equipment or an appliance, and the housing is part of a removable component. In yet other aspects of the present embodiments, the removable component may be provided with a bore, a socket, a key, a groove, or other mechanical means known in the art for coupling to a tool such as a drill bit, a saw blade, or a food mixer blade, for example.

Although limited embodiments of simple release locking mechanisms and their components have been specifically described and illustrated herein, many modifications and variations will be apparent to diose skilled in the art. For example, different spring material, different spring size, and multiple rows of springs may be used without deviating from the spirit and scope of the present embodiments. Furthermore, it is understood and contemplated that features specifically discussed for one simple release locking mechanism may be adopted for inclusion with another simple release locking mechanism, provided the functions are compatible. Accordingly, it is to be understood that the simple release locking mechanisms and their components constructed according to principles of these embodiments may be embodied other than as specifically described herein. The embodiments are also defined in the following claims.

What is claimed is:

1. A locking mechanism for use in quick-release applications, comprising:
    a housing including a longitudinal axis, a first end portion of the housing including first and second furcations defining a slot therebetween, an inner surface of the first furcation including a first groove therein:
    a piston including a body section, a first end of the body section defining first and second shoulders, a tongue extending away from the shoulders along the longitudinal axis, a surface of the tongue including a second groove therein;
    a sleeve slidably engaging an outer surface of the piston body section; and
    a canted-coil spring;
    wherein the locking mechanism comprises a first configuration in which the tongue is disposed within the slot such that the furcations abut the shoulders and the first and second grooves are aligned, the canted-coil spring is disposed within the first and second grooves and is compressed by the first and second grooves, and the sleeve is positioned over at least a portion of a junction between the housing and the piston such that the sleeve engages the outer surface of the piston body section and outer surfaces of the furcations, thereby resisting relative motion of the housing and the piston in a direction perpendicular to the longitudinal axis.

2. The locking mechanism of claim 1, wherein in the first configuration the sleeve also engages an outer surface of the tongue.

3. The locking mechanism of claim 1, wherein a surface of the body section includes a third groove therein.

4. The locking mechanism of claim 3, further comprising a second canted-coil spring disposed within the third groove.

5. The locking mechanism of claim 4, wherein the sleeve is disposed over the second canted-coil spring when the locking mechanism occupies the first configuration, and the sleeve compresses the second canted-coil spring within the third groove.

6. The locking mechanism of claim 1, wherein when viewed in cross-section a base of the first groove forms an oblique angle with, the longitudinal axis.

7. The locking mechanism of claim 6, wherein the housing includes a second end portion opposite tire first end portion, and a depth of the first groove increases with increasing distance from the second end portion.

8. The locking mechanism of claim 1, wherein when viewed in cross-section a base of the second groove forms an oblique angle with the longitudinal axis.

9. The locking mechanism of claim 8, wherein a depth of the second groove increases with increasing distance from the piston body portion.

10. The locking mechanism of claim 1, wherein the tongue includes a first portion having a relatively shorter length and a second portion having a relative longer length, and the slot includes a first portion having a relatively lesser depth and a second portion having a relatively greater depth, such, that the tongue may only be inserted completely within the slot when the tongue first portion is aligned with the slot first portion and the tongue second portion is aligned with the slot second portion.

11. The locking mechanism of claim 1, further comprising a second canted-coil spring, wherein an inner surface of the second furcation includes a third groove therein, the surface of the tongue includes a fourth groove therein, and when the locking mechanism, occupies the first configuration the third and fourth grooves are aligned, the second canted-coil spring is disposed within the third and fourth grooves and is compressed by the third and fourth grooves.

12. The locking mechanism of claim 11, wherein when viewed in cross-section, a base of the third groove forms an oblique angle with the longitudinal axis.

13. The locking mechanism of claim 12, wherein the housing includes a second end portion opposite the first end portion, and a depth of the third groove increases with increasing distance from the second end portion.

14. The locking mechanism of claim 11, wherein when viewed in cross-section a base of the fourth groove forms an oblique angle with the longitudinal axis.

15. The locking mechanism of claim 14, wherein a depth of the second groove increases with increasing distance from the piston body portion.

16. The locking mechanism of claim 1, wherein the housing further comprises a wall portion extending between the first and second furcations and forming a substantial U-shaped cross-section.

17. The locking mechanism of claim 16, wherein the first groove extends to an inner surface of the wall portion and an inner surface of the second furcation.

18. The locking mechanism of claim 1, wherein a width of the first groove is less than a height of the canted-coil spring measured along its minor axis.

19. The locking mechanism of claim 1, wherein a width of the second groove is less than a height of each coil of the canted-coil spring measured along a minor axis of the coil.

20. A locking mechanism for use in quick-release applications, comprising:
a housing including a longitudinal axis, a first end portion of the housing including first and second furcations defining a slot therebetween, an inner surface of the first furcation including a first groove therein, an inner surface of the second furcation including a second groove therein;
a piston including a body section, a first end of the body section defining first and second shoulders, a tongue extending away from the shoulders along the longitudinal axis, a surface of the tongue including a continuous perimeter groove therein;
a sleeve slidably engaging an outer surface of the piston body section; and
a canted-coil spring disposed within the continuous perimeter groove;
wherein the locking mechanism, comprises a first configuration, in which the tongue is disposed within the slot such that the furcations abut the shoulders and the continuous perimeter groove is aligned with the first and second grooves, the canted-coil spring is disposed within the first and second grooves and is compressed by the first and second grooves, and the sleeve is positioned over at least a portion of a junction between the housing and the piston such that the sleeve engages the outer surface of the piston body section and outer surfaces of the furcations, thereby preventing relative motion of the housing and the piston in a direction perpendicular to the longitudinal axis.

21. The locking mechanism of claim 20, wherein a cross-sectional shape of the tongue is circular or square.

22. The locking mechanism of claim 20, wherein a cross-sectional shape of the tongue includes straight and arcuate boundaries.

23. The locking mechanism of claim 20, wherein when viewed in cross-section a base of the continuous perimeter groove forms an oblique angle with the longitudinal axis.

24. The locking mechanism of claim 23, wherein a depth of the second groove increases with increasing distance from the piston body portion.

25. The locking mechanism of claim 20, wherein the housing further comprises a wall portion extending between the first and second furcations and forming a substantially U-shaped cross-section.

26. The locking mechanism of claim 25, wherein the first and second grooves extend to an inner surface of the wall portion.

* * * * *